(12) United States Patent
Armstrong

(10) Patent No.: US 7,214,299 B2
(45) Date of Patent: May 8, 2007

(54) METHOD FOR SEPARATION, IDENTIFICATION AND EVALUATION OF MICROBES AND CELLS

(76) Inventor: Daniel Armstrong, 3124 Almond Rd., Ames, IA (US) 50010

( * ) Notice: Subject to any disclaimer, the term of this patent is extended or adjusted under 35 U.S.C. 154(b) by 594 days.

(21) Appl. No.: 10/083,845

(22) Filed: Feb. 26, 2002

(65) Prior Publication Data

US 2002/0148729 A1 Oct. 17, 2002

Related U.S. Application Data

(63) Continuation-in-part of application No. 09/603,446, filed on Jun. 23, 2000, now abandoned.

(51) Int. Cl.
*G01N 27/447* (2006.01)

(52) U.S. Cl. ................. 204/455; 204/452; 204/451; 204/456

(58) Field of Classification Search ........ 204/451–455, 204/610, 459; 436/514–516
See application file for complete search history.

(56) References Cited

U.S. PATENT DOCUMENTS

| 4,375,401 | A | * | 3/1983 | Catsimpoolas | 204/607 |
| 4,526,865 | A | * | 7/1985 | Silman | 435/35 |
| 5,006,210 | A |   | 4/1991 | Yueng et al. | 204/452 |
| 5,108,568 | A | * | 4/1992 | Van Alstine | 204/450 |
| 5,578,460 | A |   | 11/1996 | Ebersole et al. | 435/29 |
| 5,723,031 | A |   | 3/1998 | Durr et al. | 204/451 |
| 6,033,546 | A |   | 3/2000 | Ramsey | 204/603 |
| 6,042,710 | A |   | 3/2000 | Dubrow | 204/454 |
| 6,045,676 | A |   | 4/2000 | Mathies et al. | 204/603 |
| 6,046,056 | A |   | 4/2000 | Parce et al. | 204/403.05 |
| 6,558,945 | B1 | * | 5/2003 | Kao | 435/287.2 |
| 6,613,211 | B1 | * | 9/2003 | McCormick et al. | 204/601 |
| 6,833,061 | B1 | * | 12/2004 | Fuhr et al. | 204/548 |
| 7,033,474 | B1 | * | 4/2006 | Dubrow et al. | 204/601 |

FOREIGN PATENT DOCUMENTS

FR 2468120 A * 5/1981

OTHER PUBLICATIONS

Derwent abstract of FR 2468120 A (Sabolovic et al. ).*
First page of "*Streptococcus pyogenes*" article downloaded on Feb. 2, 2005 from www.textbookofbacteriology.net/streptococcus.html.*
"The Bacteria Antibotics Can't Kill" downloaded on Feb. 2, 2005 from www.tigr.org/~btran/ENTEROCCUS.html.*
"TSCA Experimental Prelease application Approvd for *Pseudomonas putida* Strains (fact sheet)" downloaded Feb. 2, 2005 from www.epa.gov/docs/opptintr/biotech/4-5dec.htm.*

(Continued)

*Primary Examiner*—Alex Noguerola
(74) *Attorney, Agent, or Firm*—Lucas & Mercanti, LLP

(57) ABSTRACT

The method entails using capillary electrophoresis or capillary isoelectric focusing to separate intact microbes. The capillary system can be a conventional capillary tube or a microfluidic device.

The method is employed to maintain the microbes intact to identify and/or quantitate the microbes. The identification of the microbe allows for the diagnosis of disease associated with the microbe.

20 Claims, 18 Drawing Sheets

OTHER PUBLICATIONS

CAPLUS abstract of Barkas et al. ("Use of polyacrylamide gel electrophoresis for the preparation of oriented virus particle preparations," Doklady Akademii Nauk SSR (1979), 245(3), 736-9 (Biochem.).*

Liu et al. "Review: Capillary isoelectric focusing as a tool in the examination of antibodies, peptides and proteins of pharmaceutical interest," journal of Chromatography A, 735 (1996) 165-190).*

English language translation of Tollet et al. (FR2468120 A—published May 1981).*

CAPLUS abstract of Jenkins et al. (Capillary isoelecric focusing of hemoglobin variants in the clinical laboratory, Clinica Chimica Acta (1999), 289(1-2), 121-132).*

PCT International Search Report, PCTUS01/20212.

Daniel W. Armstrong, Anal. Chem. 1999, 71, 5465-5469, Separating Microbes in the Manner of Molecules.

* cited by examiner

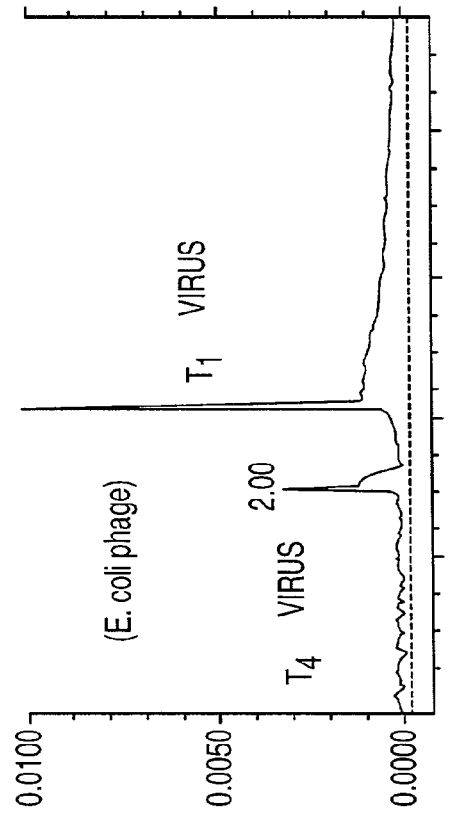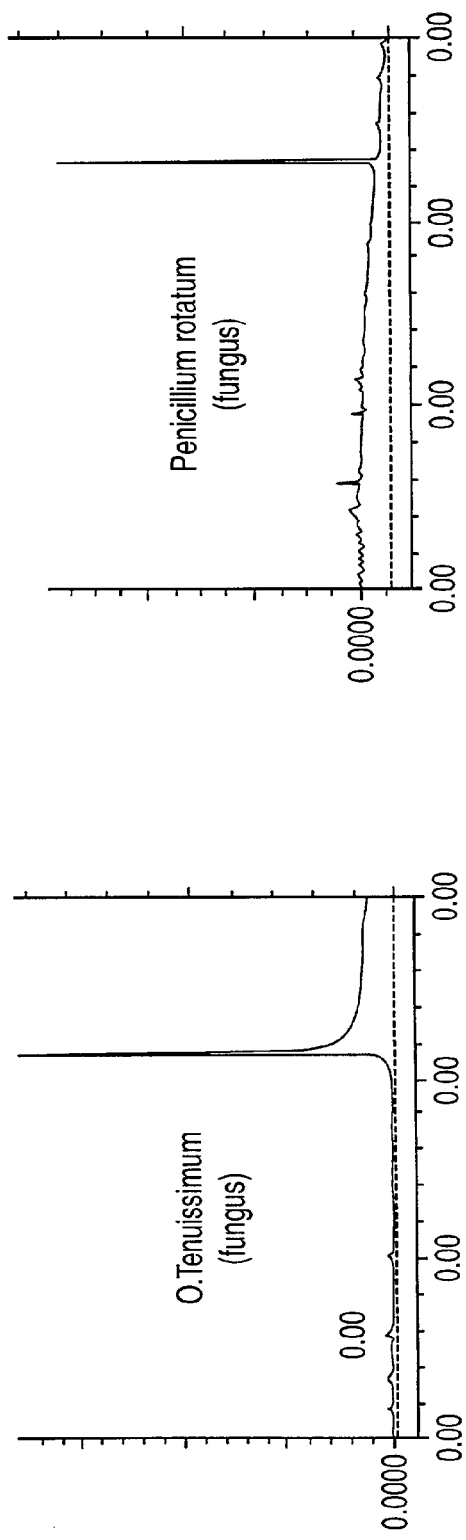

METHOD FOR SEPARATION, IDENTIFICATION AND EVALUATION OF MICROBES AND CELLS

This application is a continuation-in-part of U.S. application Ser. No. 09/603,446, filed Jun. 23, 2000, now abandoned.

BACKGROUND OF THE INVENTION

1. Field of the Invention

This invention relates to separation, identification, quantification and evaluation of intact microbes and cells by electrokinetic separation systems that employ small passageways with a fluid therein and electrical forces to cause movement in the passageway, such as capillary electrophoresis, capillary isoelectric focusing, or microchip fluidic systems. The method of the present invention is especially well suited for diagnosis of disease and for use in industries such as food, biotech and military where the presence or absence of microbes is key to an analysis.

2. Art Related to Invention

Microbes or microorganisms are small complex organic systems which are capable of reproduction, some on their own and some only in a host. They include bacteria, fungi, algae, viruses, yeast, spores, and protozoa.

The process for separation and identification of microbes is largely dominated by 19th century procedures of growing and isolating pure cultures. This is a slow and tedious process that works only for a small fraction of microbes. There are many microbes that still cannot be isolated and identified in this manner. Furthermore, such a process does not allow for the rapid differentiation between various microbes in a complex mixture nor quantification and evaluation of the microbes.

Electrokinetic separation techniques are well known. Capillary electrophoresis, capillary isoelectric focusing, isotacophoresis and gel electrophoresis are conventional techniques which are typically used to separate and isolate chemical compounds. They have never been successfully employed for separation, identification, quantification and further evaluation of intact microbes and cells.

Microchip fluidic systems are a relatively new electrokinetic separation technique. Examples of this technique can be found in U.S. Pat. No. 6,046,056 issued Apr. 4, 2000; U.S. Pat. No. 6,045,676 issued Apr. 4, 2000; U.S. Pat. No. 6,042,710 issued Mar. 28, 2000; and U.S. Pat. No. 6,033,546 issued Mar. 7, 2000. The devices employed in microchip fluidic systems are often referred to as microchip capillary devices, microfabricated devices, and microfluidic devices. Such devices are usually made from silicon, quartz, glass or polymers such as poly(dimethylsiloxane). In essence, they are miniaturized capillary systems which have a number of advantages over conventional capillary systems, the primary one being size.

Electrokinetic techniques have been employed to analyze the contents of lysed cells, however, these methods have not proven to work with lysed microbes and mixtures of lysed microbes to allow unambiguous identification of microbes. One of the problems is that different microbes often have similar intracellular structures, thus once the microbe is lysed, each microbe looks alike.

There is a need for a simple, quick analytical technique which would allow for separation, identification, quantification and evaluation of microbes.

SUMMARY OF THE INVENTION

It has now been discovered that microbes and cells can be both separated, identified, quantified and evaluated using an electrokinetic process if the microbe/cell remains intact. The microbe/cell can be alive or dead, so long as it is not lysed, i.e. remains physically intact. The present invention allows for fast and accurate identification of microbes/cells. This process can also be used to identify diseases caused by the microbes or in any industry where the identification of microbes, the presence or absence of a microbe, and the number, quantity, of microbes present, is key to an analysis. Such a process can be used, for instance, in the food industry, medical industry, biotechnology industry, and for military applications.

Additionally, the viability of the microbe/cell can be determined. Thus, not only can the microbes/cells be separated, and quantitated, but also the percent live and dead determined in a single run.

Furthermore, it has been found that the microbe/cell can be evaluated for its binding affinity with drugs or other substances. The binding affinity can be determined in accordance with the present invention because the drug/other substance with or without the microbe/cell acts differently in the electric field. Additionally, the degree of binding has also been found to effect the way the drug/other substances and microbe/cell moves in the electric field.

Broadly, the process of the present invention comprises:

obtaining a sample containing one or more intact microbes/cells from a substrate containing said microbes/cells;

introducing said sample into a passageway having a fluid therein;

separating said one or more microbes/cells in said fluid by means of an electric field so as to cause said one or more microbes/cells to move in said fluid and to separate one from another and from any other components in said sample while maintaining said microbes/cells intact; and analyzing said separated intact microbes/cells in order to identify and/or quantify and/or evaluate the microbe/cell.

The substrate can vary depending on the industry. For example, in the food industry, the substrate will be a foodstuff, say raw meat, and the microbe which is identified can be in the genus salmonella. In this example, the analysis step would result in associating the salmonella bacteria with the problem that such a bacteria can cause, namely, food poisoning or salmonellosis.

In the case of a binding affinity, the substrate can be a mixture of the microbe and drug/other substance. For example, a microbe and an antibiotic are mixed together and the level of binding associated with known levels of binding to determine if the antibiotic is effective against the microbe and the degree of effectiveness.

The analysis step can include an association step wherein the microbe/cell which has been identified by the analysis is associated with stored data of affects known to be caused by the microbe, e.g. associating the microbe with a known disease that it causes. Such stored data is conventionally done in a computer.

In one embodiment, the process of the present invention is a method for separating and identifying intact microbes/cells present in a substrate.

The analysis step can include a quantification step, such that the number of microbes/cells present in the sample is also determined.

The sample of intact microbes/cells need not be pure. In other words, it can be a group of homogeneous microbes/ cells, as well as a group of heterogeneous microbes/cells, e.g. a mixture of different microbes. Also, there can be other components such as molecules, chemicals, or non-microbial/non-cellular components in the sample. For example, the sample could contain plant skin scrapings, human skin scrapings, soil, human or animal body fluids. The sample can also be diluted with a solvent to facilitate injection into and separation in the passageway.

Suitably, the passageway is a small channelway such as a conventional capillary tube, e.g. a fused silica capillary tube or a fluid capillary device such as the type used in a microchip capillary system. As is understood by those of skill in the art, capillary tubes and microchip capillary systems can have a variety of different cross sectional shapes and lengths. Each is, in essence, a passageway having fluid therein.

Suitably, capillary electrophoresis or capillary isoelectric focusing is used to separate the microbes, one from another, and to separate the microbes from the other components in the sample.

Analysis of the microbe/cell, in order to determine which microbe/cell or microbes/cells are present, is done using conventional analytical techniques which are associated with electrokinetics. For example, optical recognition, mass spectrometry, or electrochemical means. These processes are operated in a conventional manner on the microbes/cells using conventional equipment, once the microbes/cells have been separated one from another and from any other components that are present in the sample. Additionally, antibodies or genetic markers can be used to analyze and identify microbes.

Quantification of the microbes/cells is also possible with these standard techniques. Conventional analytical techniques employed with electrokinetics generally provide a degree of magnitude for the components in a sample. Such is conducted in a conventional manner using conventional equipment.

The process for determining the binding affinity of a drug, protein, prion, or other substance to a microbe/cell in accordance with the present invention, after obtaining a sample containing intact microbes/cells, the sample is combined with a drug or other substance in a fluid media to form a suspension and to allow said microbe/cell to bind with said drug/other substance.

The analysis of the separated, intact bound microbes/cells-drug/other substance to determine their affinity for each other is done by any of the common capillary electrophoresis (CE) methods including: frontal analysis, vacancy peak method, affinity CE, partial-filling, direct separation, or Hummel-Dreyer methods.

Such analysis is conducted in a conventional manner, such as by comparing the results against a previously measured standard. Other substances which can be tested for their binding affinity with microbes/cells include pathogens such as prions and especially prion protein scrapie.

The separation step requires the microbe/cell to be in a fluid medium in the passageway in order to allow for movement of the microbe/cell. Thus, the sample can provide the fluid to the passageway or the passageway can have fluid in it prior to introducing the sample into the passageway.

The process for diagnosing a disease caused by a microbe or microbes in accordance with the present invention includes associating said microbes with a disease so as to diagnose said disease.

The organism stricken with the disease (infected) can be either animal or plant The sample can be, for example, plant or animal and, more specifically, plant skin, animal skin, internal plant fluids, or internal animal fluids. For example, it could be human blood. As pointed out above, the sample can contain other, non-microbial components, such as chemicals, molecules, etc.

The sample containing microbes can be directly injected or can be pretreated before injecting. Pretreatments can make certain microbes easier to separate or detect. For example, one specific microbe, in the presence of others, can be pretreated to make it fluorescent and thereby easier to detect with a fluorescence detector. Another example is to pretreat or label a microbe with a compound of specific mass and would make it easier to detect with a mass spectrometer. The pretreatment generally comprises a brief washing or soaking of the microbe in a buffed solution of a specific chemical or chemicals. Another example of a non-chemical pretreatment is brief (approximately 3 min.) sonification of the microbes to breakup their aggregates, as described below. Pretreatment should be such as to avoid or suppress aggressive behavior between microbes as well as to avoid aggregation and maintain the microbe intact.

Also, one of skill in the art will recognize that the sample may need to be diluted with a liquid solution that is compatible with the fluid in the passageway so as to avoid overcrowding the passageway and to allow for efficient separation of the microbes, one from another and from any other components that are present in the sample. Such sample preparation is conventional and well known to those of skill in the art. The liquid solution must also be such that it does not lyse the microbe/cell.

Additionally, it has been found that microbes do not behave like conventional molecules. For example, two or more different microbes in solution tend to interact with each other or release chemicals into solution to attack or lyse the other microbe. Alternatively, they can try to stick to one another. Steps must be taken to maintain the integrity of the microbe and prevent or suppress these actions long enough to obtain a separation and analysis in accordance with the present invention.

Association of the microbes with a disease is done by comparing the microbes against diseases which it is known to cause. Suitably, a computer processor is used to make this comparison based on stored data and the data obtained by analyzing the separated microbes and identifying the separated microbes.

It has been found that the separation is based on size, shape, outer configurations and composition of the microbe/cell, and the isoelectric point of the microbe/cell.

Microbes such as bacteria, viruses and fungi have a surface charge that originates from the ionization of the surface molecules and/or the adsorption of ions from solution. They have membranes and cells which contain protein, lipopolysaccharides, lipid molecules, teichoic acid, etc. which gives the microbes a characteristic charge. This charge will vary with pH, solution composition, ionic strength and temperature. All of this must be taken into consideration in the present invention, especially when determining the viablity of the microbe in accordance with the present invention.

Specific dyes can selectively associate with, or be excluded from live and/or dead cells. For example, trypan blue stains non-viable cells with compromised membranes, but does not stain viable cells. There are a variety of fluorescent nucleic acid and membrane-based dyes. They are used in accordance with the present invention alone or in specific combinations to assess cell viability and other cell functions. After the chosen staining procedure is completed, the stained cells are introduced as the sample in the process of the present invention.

It is important to take the necessary precautions to maintain the microbes/cells intact and to prevent them from lysing when preparing the sample and when separating the sample in the passageway. The microbes/cells can be alive or dead, provided they have not become lysed. In preparation of the sample for introducing it into the passageway, some of the microbes/cells may become lysed, however, precautions should be taken to prevent lysing of the microbes/cells, because lysed microbes/cells cannot be properly separated and effectively identified by the present invention. This means that the chemical makeup of the various buffers, analytes and solutions used as well as the electric conditions during electrokinetic separation must be such that the microbes/cells are not lysed and remain intact. In the past, microbes/cells have been lysed and their contents analyzed. This has not proven to be an effective or efficient way to analyze or differentiate between different microbes/cells.

As will be recognized by those of skill in the art, mass spectroscometry can destroy the microbe/cell. This, however, is conducted after the microbes/cells have been separated and is part of the analysis step.

Besides disease diagnosis, the present invention can be used in a number of other areas where microbes/cells are encountered and where their identification and quantification is desired. For example, identification of unwanted pathogens in water (e.g. drinking water, sewage or treatment facility ponds, and cooling tower water supplies were legionella (legionnaire's disease) grows), germ warfare, environmental control and pollution detection, bioremediation, assays for products that contain microbes, fermentation, food processing, biotechnology, soil monitoring and purification, agriculture, animal husbandry and veterinary science, study of microbes, study of microbe spores, and spore formation, to name a few.

Also, the process of the present invention provides for unknown microbes/cells to be easily seen and isolated using the same procedure. These unknown microbes/cells can be identified by other means (e.g, DNA testing) or held for future identification or left unknown.

The present invention is also directed to an improved microfluidic device having an injector, a passageway, a detector, and a CPU, wherein the improvement comprising said detector is a Mei light scattering apparatus or a laser induced fluorescence apparatus for detecting microbes/cells.

The improved microfluidic device preferably has its passageway washed with a suspension of intact microbes/cells before conducting the detection.

The improved microfluidic device can employ a fluorescent dye to detect the viability of intact microbes/cells.

Microfluidic devices have not, in the past, employed a Mei light scattering detector, have not been washed with a suspension of microbes/cells before, employed fluorescent dyes to detect viable microbes/cells nor been used with intact microbes/cells.

These and other aspects of the present invention may be more fully understood by reference to one or more of the following drawings.

BRIEF DESCRIPTION OF THE DRAWINGS

FIG. 7 illustrates an electropherogram of a mixture of intact viruses separated and identified in accordance with the present invention using CE;

FIG. 8A illustrates an electropherogram of an intact *Oidiodenron tenuissmum* identified in accordance with the present invention using CE;

FIG. 8B illustrates an electropherogram of an intact *Penicillium rotatum* identified in accordance with the present invention using CE;

DETAILED DESCRIPTION OF THE INVENTION

Figure 1A:
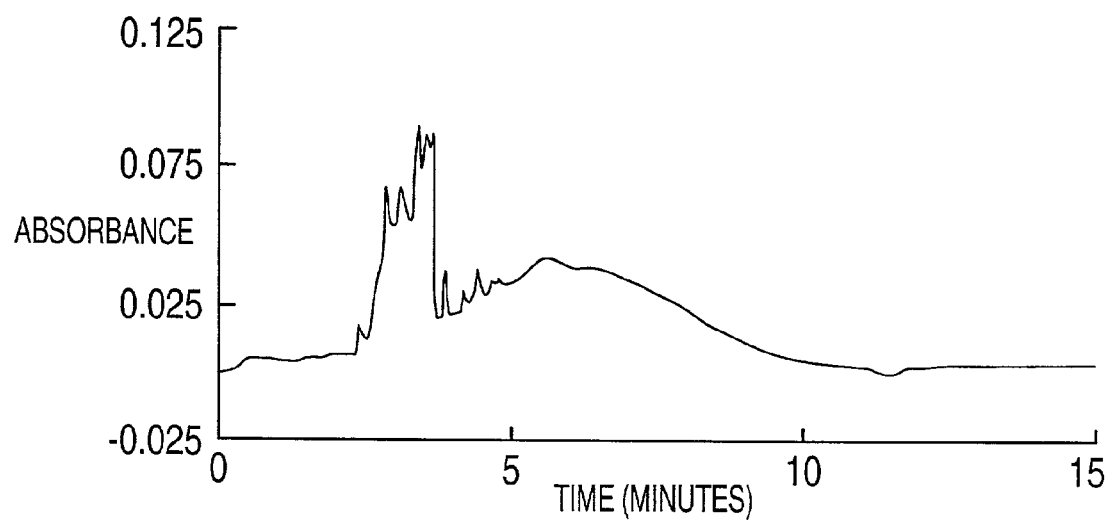
FIG. 1A illustrates an electropherogram of lysed *P. fluorescens* using capillary electrophoresis (CE)

Obtaining a sample containing the microbes/cells and preparation of the sample for introduction into the passageway is conducted in a conventional manner using conventional equipment provided precautions are taken not to lyse or destroy the microbe/cell. For example, blood is drawn from a human with a syringe and then diluted and/or pretreated in a conventional manner. The pH, concentration and other characteristics of the solvent must be such that it does not lyse or destroy the microbes/cells and aids in suppressing the aggressive behavior or deleterious passive behavior between the microbes.

The passageway employed is a conventional channel employed in electrokinetic devices such as capillary tubes or microfluidic devices. For example, fused silica capillary tubes are employed in capillary electrophoresis.

The preferred fluid employed in the passageway is water or a water-based solution. Microbes are generally stable in properly buffered water of proper ionic strength and, therefore, are not lysed. The fluid must be compatible with the microbes/cells, be non-detrimental to microbe/cell mobility and assist in suppressing aggressive behavior between microbes/cells as well as being properly buffered, having a proper pH and proper concentration so as to avoid lysing the microbes/cells and promote separation and good mobility of the microbes.

The device and system used for the process of the present invention is suitably a conventional device used for capillary electrphoresis, capillary isoelectric focusing or microfluidic devices. These devices are run in a conventional manner except as noted herein.

When employing capillary electrophoresis, a water soluble polymer must be present. The polymer should have a molecular weight of at least about 5,000 Daltons and, more preferably, about 10,000 to about 10,000,000 Daltons or higher. Suitable polymers include polyethylene oxide (PEO), polyethylene glycol (PEG), polyvinyl alcohol, linear polyacrylamide, polyvinylpyrrolidone (PVP), hydroxypropylcellulose (HPC), hydroxyethylcellulose (HEC), methylcellulose (MC), amylose and dextrin.

In general, the polymer must be soluble and/or dispersible in aqueous solution, i.e. the fluid inside the passageway. The type of polymer, its molecular weight distribution, and its concentration in solution effect the separation. Generally, for microbes/cells, the concentration of polymer needed is less than that which is conventionally used for protein, DNA, and RNA fragment separation. For microbes/cells that are large in size, a lower concentration of polymer is preferred. Routine testing can be conducted to optimize the best concentration, molecular weight distribution and type of polymer for a specific microbe/cell or microbial mixture. Furthermore, it has been found that the migration times and the mobility or migration time of the microbe/cell in the fluid can be varied by varying the concentration, molecular weight distribution and type of polymer employed in the fluid.

The capillary electrophoresis or microfluidic device with water soluble polymer present in the fluid, i.e. the running buffer, is operated in a conventional manner using conventional equipment.

The capillary isoelectric focusing has an ampholyte that is chosen specifically for focusing the microbe/cell in the fluid and will not lyse the microbe. The ampholyte has a pH of 3 to 13 and is chosen based on the microbe/cell or microbes/cells to be separated. The capillary isoelectric focusing is conducted in a conventional manner using conventional equipment. The ampholyte is chosen so as to avoid lysing the microbe/cell, maintain the microbe/cell intact, avoid or suppress aggressive behavior between microbes/cells and to allow for efficient focusing of the microbe/cell.

When employing the present invention, the concentration of the microbes/cells in the solution or suspension should be such as to allow for separation, and avoid aggregation and aggressive behavior between the microbe/cell. Also, the amount of the injection of the sample into the column should not be too large or else it can result in two peaks for the same materials. For example, with a 78 second, 0.5 psi capillary tube, an injection of about 5 to about 10 seconds at about 0.5 psi is good, while an injection of about 20 to about 30 seconds at about 0.5 psi can result in two or more peaks, not one. Good results have been obtained when the volume of the injection of the sample to be processed in accordance with the present invention is equal to about 5 to about 20 percent of the internal volume of the capillary tube and, more particularly, a volume of about 10 to about 15 percent of the internal volume of the capillary tube.

The solution itself, or buffer, is chosen to promote movement of the microbes/cells, avoid lysing or destruction of the microbes/cells, avoid aggregation and aggressive behavior between the microbes/cells. In the case of sperm, this means avoid destroying the viability of the sperm and, in the case of prions, avoid denaturing the three-dimensional structure of the prion.

The voltage employed in both capillary electrophoresis and capillary isoelectric focusing must be such that it promotes electrophoretic mobility. The optimum voltage will vary from microbe/cell to microbe/cell.

FIGS. 1–10, 12 and 13 illustrate the process of the present invention. They will be discussed in more detail in the examples that follow.

Figure 11:
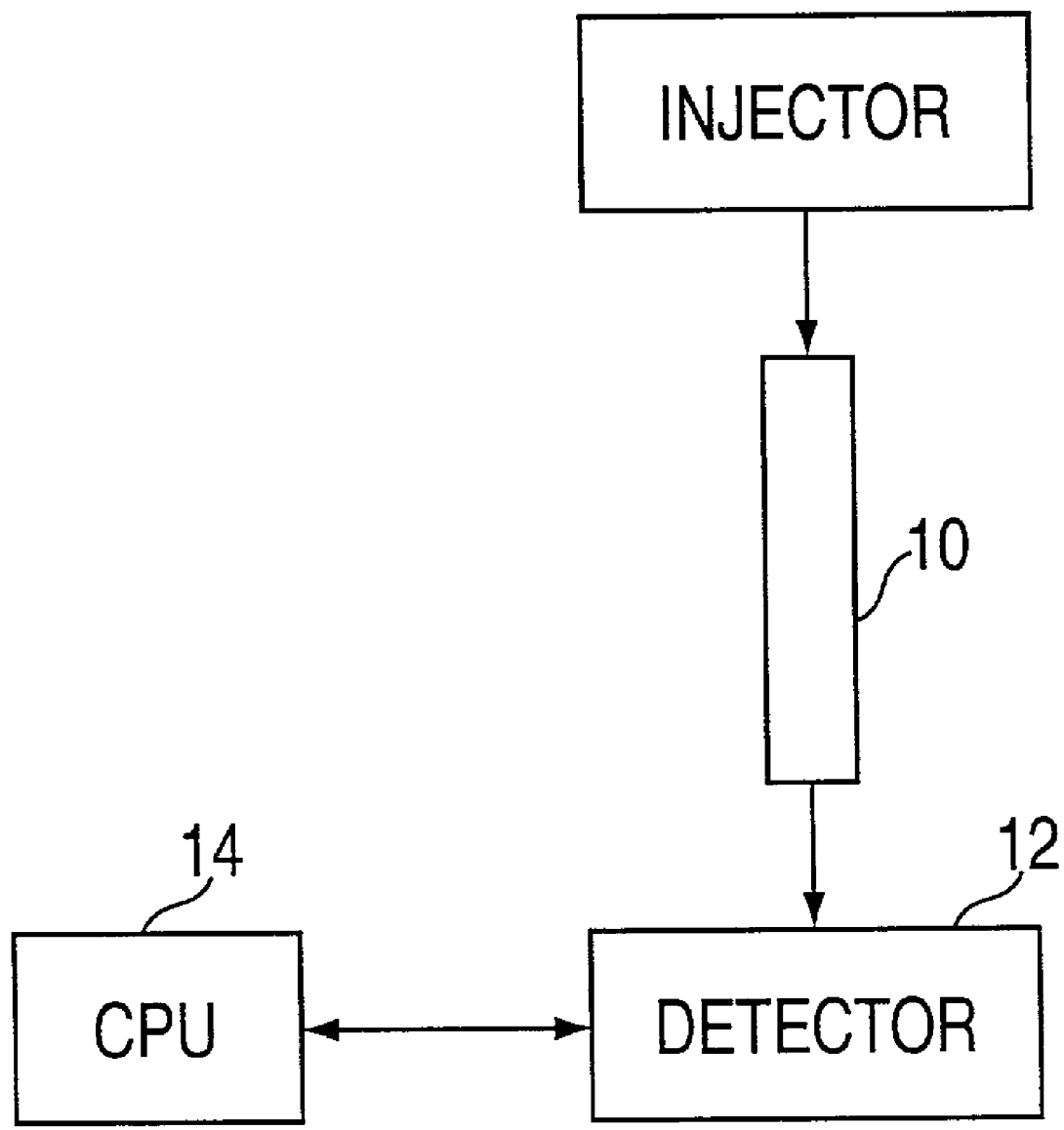
FIG. 11 illustrates an apparatus which can be used in the present invention.

FIG. 11 illustrates an apparatus which can be employed for use in the process of the present invention.

As shown in FIG. 11, the apparatus which can be used in the present invention comprises capillary tube system or passageway 10 of microfluidic chip device and the associated hardware for the isoelectric focusing electrophoresis. Detector 12 is connected at one side of the passageway system. Detector 12 is connected to CPU 14 for analyzing the separated microbe/cell so as to identify the microbe/cell and associate the microbe/cell with its known consequences, e.g. a disease. Such a device is operated in a conventional manner. Where detector 12 is a mass spectrometer, a conventional interface is employed between column 10 and detector 12. Such an interface is operated in a conventional manner.

The improved microfluidic device of the present invention is operated in a conventional manner except that detector 12 is a Mei light scattering device or a laser induced fluorescence apparatus. Such a detector is used because of the size of the microbes/cells. Such a device is operated in a conventional manner using conventional equipment.

The devices used in accordance with the present invention can be optimized for a specific microbe/cell as disclosed hereinbelow or optimized for microbes/cells in general by adjusting the geometry of the passageway, the interface betweeen the passageway and the detector, or adding an optical device, such as a microscope, to view the microbes/cells in the system, e.g. to view the microbes/cells in the injection fluid, the passageway, or after detection.

Microbes which are suitable for separation and identification in accordance with the present invention include bacteria, spores, fungus, algae, virus, yeast, and protozoa. Specific examples are:

| Bacteria | |
|---|---|
| Alcaligenes faecalis | Bacillus cereus |
| Bacillus megaterium | Bacillus subtilus |
| Corynebaterium diphtheria | Esterobacter aerogenes |
| Enterobacter cloacae | E. coli: K12 |
| E. coli: ATCC#11303 | E. coli: ATCC#9637 |
| E. coli: ATC#23499 | E. coli: ATCC#23500 |
| E. coli: ATCC#23501 | Lactobacillus plantarum |
| Micrococcus luteus | Pseudomonas aeraginosa |
| Pseudomonas fluorescens | Salmonella typhimurium |
| Serratia rubidae | Staphylococcus aureus |
| Staphylococcus epidermis | Pseudomonas putida |
| Proteus miralis | Streptococcus thermophilus |
| Proteus valgaris | Serratia macrcescens |
| Staphylococcus saprophyticas | Lactobacillus acidophilus |
| Lactobacillus bulgaricus | Bifidobacterium bifidum |
| Bifidobacterium infantis | |

| Fungi | |
|---|---|
| Aspergillus carbonarius | Oidiodenron tenuissmum |
| Penicillium rotatum | Fonsecaea pedrosoi |
| Saccharomyces cerevisiae | Rhizopus stolonifer |
| Fusarium oxysporum | Aspergillus ridulans |
| Penicillium chrysogenum | Aspergillus niger |
| Aspergillus ficuum | Oidiodendron tenuissinum |
| Gliomastix murorum | Penicillium ourantiogrisum |
| Penicillium crustosum | Penicillium citrinum |
| Fusarium oxysporum f. sp. lycopersici | |
| Candida albicans | |

| Algae | |
|---|---|
| Tetrahyrmena thermophila | Trichomitus batrachorum |
| Blastocrithidia culicis | Chlorella protothecoides |
| Chlorella saccharophila | Botrydium becherianum |
| Crucigenia apiculata | Blastocrithidia leptocoridis |
| Chlorella vulgaris | Botrydium stoloniferum |

Viruses

E. coli Phage PHI x 174
E. coli Phage 11303-B39
E. coli Phage 11303-B1 (T1)
E. coli Phage 23724-B2 Lambda Standard
E. coli Phage 25298-B1

Misc.

| | |
|---|---|
| Giardia muris | Cyrptosporidium parvium |

Cells which are suitable for separation and identification in accordance with the present invention include:

Sperm, and blood cells.

In order to analyze and identify the separated microbes/cells, a standard is needed, as is true for all electrokinetic techniques. Such standards are obtained in a conventional manner using conventional techniques. Once the standard is obtained, the results from the analysis step are compared to the standard and a conclusion is reached. The same holds true for diagnosis of the disease.

Typically, a series of standards are determined so that a library of standards is obtained. This library of standards is suitably stored in a computer and the computer compares the test results to the library to obtain the identification. Such is done in a conventional manner using conventional equipment.

The microbe/cell must be associated with the disease and the standard for that microbe/cell must be known. Then, once the process of the present invention is run, the test results of the process are compared to the standards so as to determine which microbe/cell is present in the sample. Then, the microbe is compared to the known microbes-disease association to determine the disease.

In the case of unknown microbes/cells, there is no match available in the library and, thus, they must be further analyzed in another known manner to determine its identity.

It is also within the scope of the present invention that the device of the present invention be adapted to test or detect the presence or absence of a single microbe/cell, i.e. a single use device. Testing for a single microbe/cell is conventional in the medical field. There are a number of single or one time tests that are employed to determine if a patient has a disease. For example, to determine whether a patient has strep throat, it is conventional for a sample to be taken from the throat of the patient and then the sample is cultured for a period of time to determine the presence or absence of the microbe, i.e. Bacterial *Streptococcus*.

In the present invention, a microfluidic device is prepared to detect the presence of the *streptococcus* bacteria only. A sample is taken from a patient's throat, prepared and injected into the microfluidic device. Then, within a matter of minutes, the presence or absence of the bacteria is detected and the patient is treated on the spot, without the need for the delay caused by culturing. Such a device can be used in other areas as well. For example, in the food industry, a single use device made in accordance with the present invention tests for salmonella bacteria only in a sample taken from a foodstuff, e.g. raw meat. In germ warfare, as ground troops move into a new area, the substrate can be soil and the troops take a soil sample and use a single use device made in accordance with the present invention to test for the presence of known pathogens, such as spores of bacteria.

The use of the present invention to detect the presence or absence of a single microbe/cell can also be used to test for the viability of sperm cells by first staining the sperm cell with a dye that binds to viable sperm cells only or one that binds to non-viable sperm cells and then subjects a sample of the dyed sperm cells to a microfluidic device employing the process of the present invention.

These and other aspects of the present invention may be more fully understood by reference to one or more of the following examples.

Microbe Preparation

For the following experiments, 7 microbes, 6 bacteria and 1 fungus (yeast) were employed. The bacteria were: (1) *Escherichia coli* K12 which produces a gram negative stain, had a diameter of 1.1–1.5 µm, was in the form of straight rods with peritrichous flagella or non mobile; (2) *Pseudomonas putida* which was gram negative, 0.5–1 µm in diameter, slightly curved rods in form, and had one or more flagella; (3) *Pseudomonas fluorescens*, gram negative stain, 0.5–1 µm diameter, slightly curved rod form, and one or more flagella; (4) *Serratia rubidae*, gram negative stain, 0.5–0.8 µm diameter, straight rod form, and *peritrichous flagella*; (5) *Enterobacteria aerogenes*, gram negative stain, 0.6–1 µm diameter, straight rod form with 4–6 *peritrichous flagella*; and (6) *Micrococcus luteus*, gram positive stain, 1–2 µm diameter, irregular clusters of cocci and non motile. The fungus was a conventional bakers yeast, *Saccharomyces cerevisiae*.

In order to obtain a sample, Bacteria 1, 2, 4 were started on solid agar, then transferred to Nutrient Broth and then grown for 24–36 hours at 25–30° C. The other microbes were purchased from a conventional source and checked before use to insure viability.

EXAMPLE 1

This example illustrates that intact microbes when subjected to capillary electrophoresis can be separated while lysed microbes cannot be efficiently and unambiguously separated.

Figure 1B:
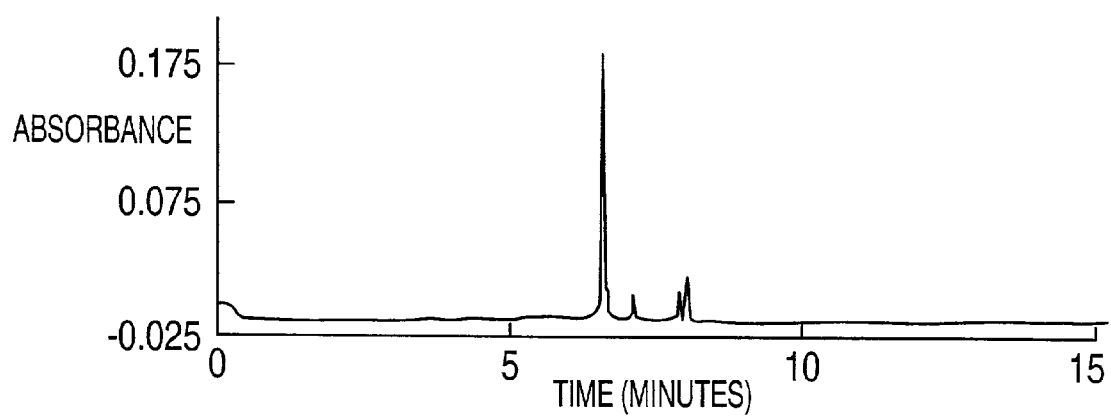
FIG. 1B illustrates an electropherogram of intact *P. fluorescens* using CE.

FIG. 1A illustrates capillary electrophoresis of a lysed *P. fluorescens* while FIG. 1B illustrates the same technique with the intact bacteria, tr=6.6 min. The various peaks in FIG. 1A represent the various proteins, protein conjugates, polynucleotides, cell fragments, etc. from the lysed cell. In contrast, as shown in FIG. 1B, the intact microbe when subjected to the same conditions, demonstrate efficiency (a sharp peak), which is easily identified. Also, because of the efficiency, the microbe can be quantified. Attempts have been made to use the cells contents, i.e. lysed cells, to identify the microbe, but the results are inconsistent and difficult to interpret, as evidenced by the electropherogram in FIG. 1A.

The *P. fluorescens* used in this example were bacteria 3 above. The capillary electrophoresis was run using a stock buffer solution containing 4.5 mM tris(hydroxymethyl)aminomethane, 4.5 mM boric acid and 0.1 mM EDTA (disodium ethylenediaminetetracetate) prepared by dissolving the appropriate amounts of each reagent in deionized water to yield a buffer of pH 8.4. The buffer was then diluted 8:1 with deionized water.

A polymer solution was prepared by adding 0.2 g of polyethylene oxide, Mn=600,000 (PEO) to 40 mL of the diluted buffer solution to give a final concentration of PEO of 0.5%. To completely dissolve this heterogeneous polymer solution, it was placed in an ultrasound bath (Fischer Model FS-28, 720W at 43 KHz) for 4 hours at about 55° C., then allowed to stand overnight. It should be noted that the sonic bath helps to hasten the dissolution of the polymer, however, too much can cause the polymer to degrade, thereby shifting the peaks. The use of the sonic bath, however, is not necessary, but it helps to hasten dissolution.

The bacterium cells were added to the dilute stock buffer to provide a concentration of 1 mg/ml. This produced a turbid solution. Thus, the solution was centrifuged, the supernatant decanted and fresh dilute buffer added to wash the cells.

The capillary electrophoresis was run using a Beckman P/ACE 2100 coupled to a computer equipped with Gold data acquisition software. Fused-silica capillary tubes with a 100 μm i.d. were used.

A running buffer was prepared by diluting the polymer solution with the diluted buffer to provide a final polymer concentration of 0.0125%. The column was 27 cm in length, 20 cm window. Prior to each run, the column was washed for 1.5 min with 0.5 N phosphoric acid, 0.5 min with water, 1.5 min with 1 N KOH, and 0.5 min with water, followed by 1 min with running buffer. The bacterium samples were pressure injected for 8–10 s. The separation voltage was 10 KV at a temperature of 23° C. On-line detection of the bacterium was done at 214 nm.

The lysed cells were prepared by warming them with 0.15% sodium dodecyl sulfate prior to injection.

The RSD (n=4) for the intact *P. fluorescens* was 2.0%.

EXAMPLE 2

This example illustrates separation and identification of intact microbes from a mixture thereof, and specifically a mixture of bacteria and fungus.

Figure 2:
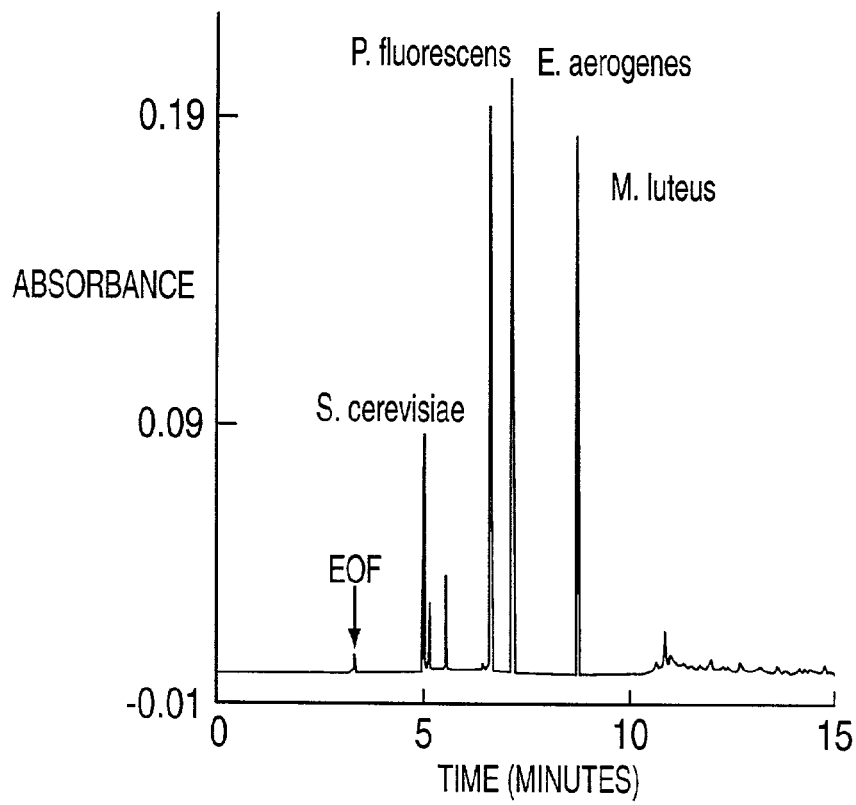
FIG. 2 illustrates an electropherogram of a mixture of intact microbes, separated and identified in accordance with the present invention using CE.

FIG. 2 illustrates the separation of microbes from a mixture of bacteria and fungus. As can be seen in FIG. 2, the process of the present invention provide for efficient and selective separation of a mixture of microbes comprising *S. cerevisiae, P. fluorescens, E. aerogenes*, and *M. luteus* into each of the individual microbes. Because of this efficiency, selectivity, and reproducibility (compare FIG. 1B to FIG. 2), the microbes were able to be identified and quantified. Each peak has been labelled with the respective microbe.

It should be noted that the earliest peak, closest to the beginning of the electroosmotic flow (EOF) was the fungus, *S. cerevisiae*, and was the largest of the microbes. The other three microbes, all bacteria, were close in size (diameter) but not in form, yet they eluted afterwards.

Furthermore, it should be noted that this separation occurred in under ten minutes and had efficiencies approaching 900,000 plates/m.

The samples and procedure used in this example were the same as that employed in Example 1 above. The microbes were those identified above under the Microbe Preparation heading. The EOF marker was mesityl oxide. The RSD's (n=4) were *S. cerevisiae* 1.8%, *M. luteus* 1.5%, and *E. aerogenes* 1.9%.

It was noted that the test tubes containing the *S. cerevisiae* and *M. luteus* had clusters of cells. Since the present invention is dependent upon having the cells dispersed, the sample test tubes were placed in an ultrasound bath (Fisher Scientific Model FS-28) at room temperature for three minutes. This served to disperse the cells which had aggregated. These cells were checked before the test to insure they were still intact.

EXAMPLE 3

This example illustrates the effect of the concentration of polymer in the buffer for capillary electrophoresis for both the running buffer itself and the microbes.

Figure 3:
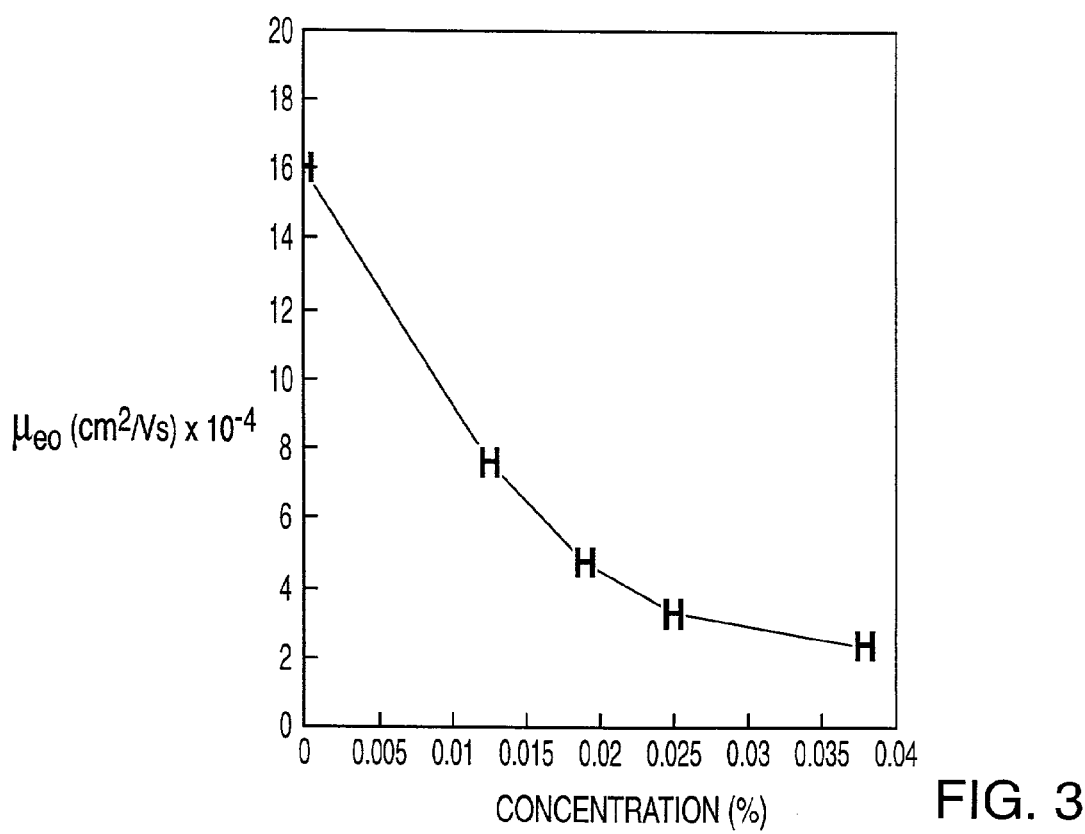
FIG. 3 illustrates the effect of polymer concentration in the running buffer versus electroosmotic velocity of the running buffer in CE.
Figure 4:
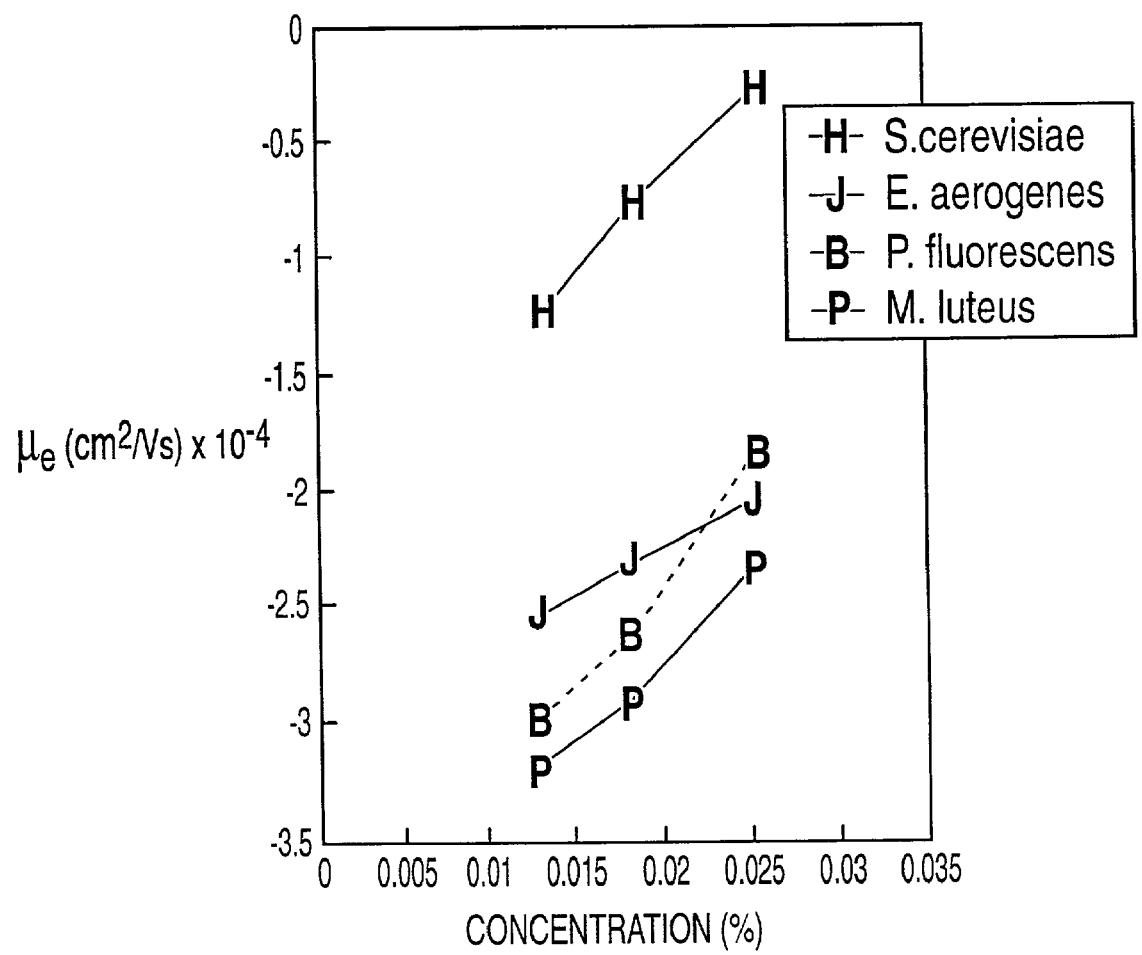
FIG. 4 illustrates the effect of polymer concentration in the running buffer versus electrophoretic mobility of intact microbes in CE.

FIG. 3 illustrates the decrease in velocity of the EOF with increased concentration of the polymer in the running buffer, while FIG. 4 illustrates the affect on migration of various microbes versus concentration of polymer. As can be seen, increased polymer concentration produced longer migration times and different electrophoretic mobility for each microbe. The polymer concentration can be varied in order to optimize the separation of microbes, one from another, or the separation of microbes from the non-microbe components in the sample or both.

With respect to FIG. 4, it should be noted that the curves are not parallel to one another, thereby allowing for different elution orders at different concentrations of polymer.

This example was run using the same procedure as Example 1 above, except the concentration of PEO in the running buffer was varied as shown in FIGS. 3 and 4 (0.015, 0.02 and 0.025). The microbes were those identified above under the heading Microbe Preparation, i.e. *S. cerevisiae, E. aerogenes, P. fluorescenes*, and *M. luteus*. The EOF marker was mesityl oxide.

EXAMPLE 4

This example illustrates the importance of having dispersed microbes, i.e. not clustered or branched.

Figure 5A:
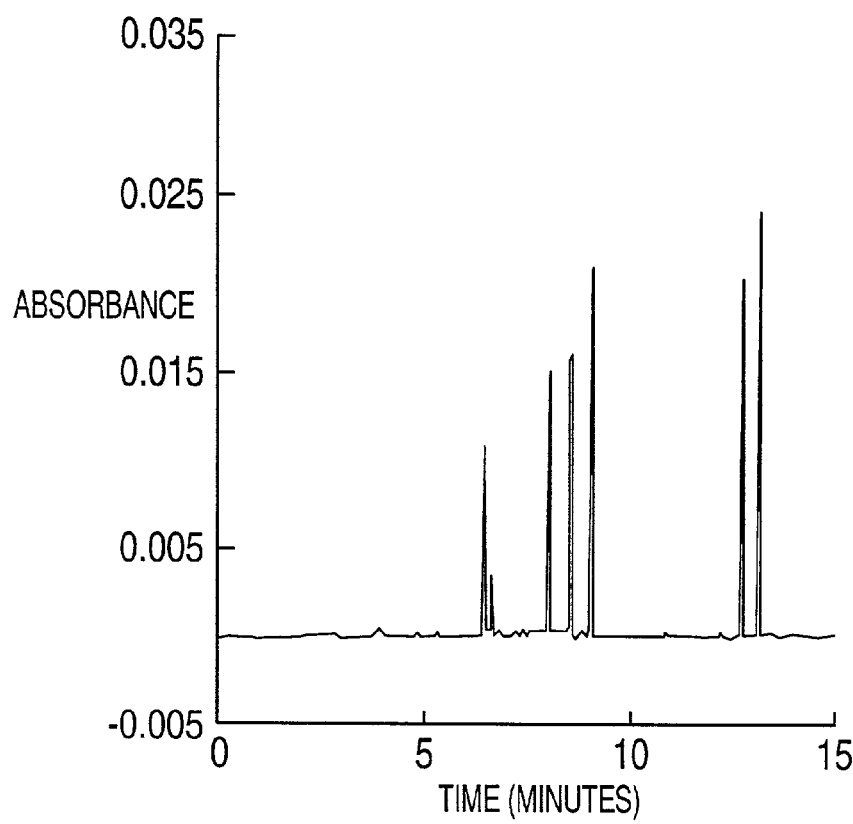
FIG. 5A illustrates an electropherogram of intact, aggregated *M. luteus* using CE.
Figure 5B:
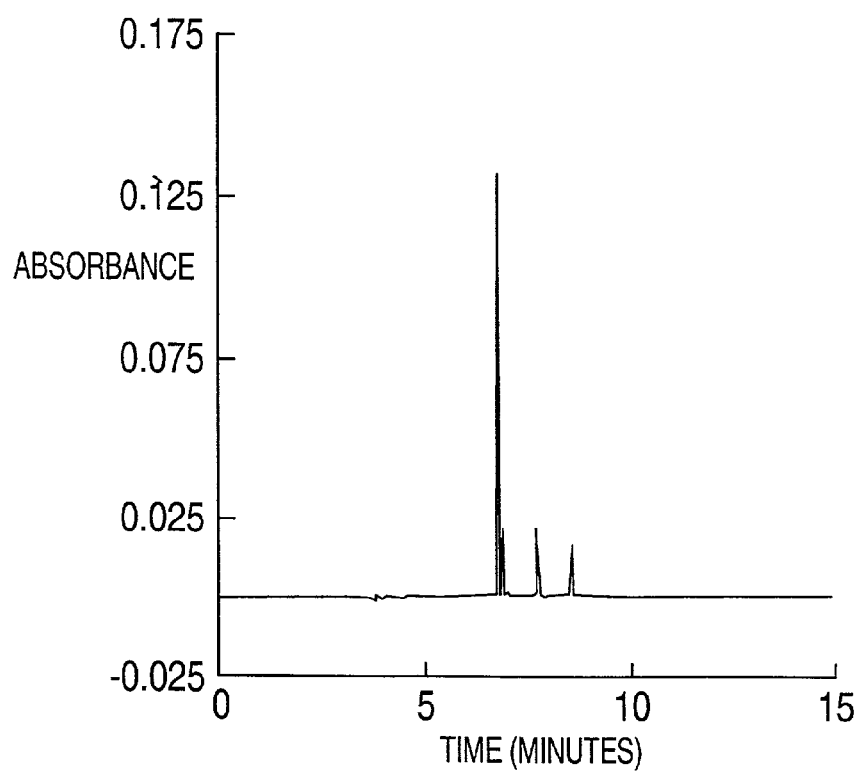
FIG. 5B illustrates an electropherogram of intact, dispersed *M. luteus* using CE.
Figure 6A:
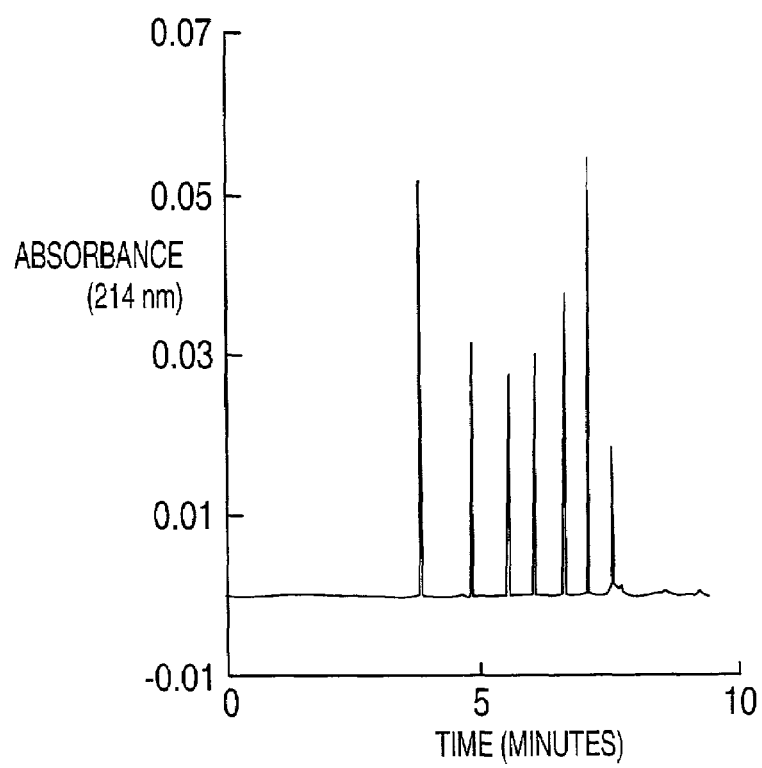
FIG. 6A illustrates an electropherogram of intact, aggregate *S. cerevisiae* using CE.
Figure 6B:
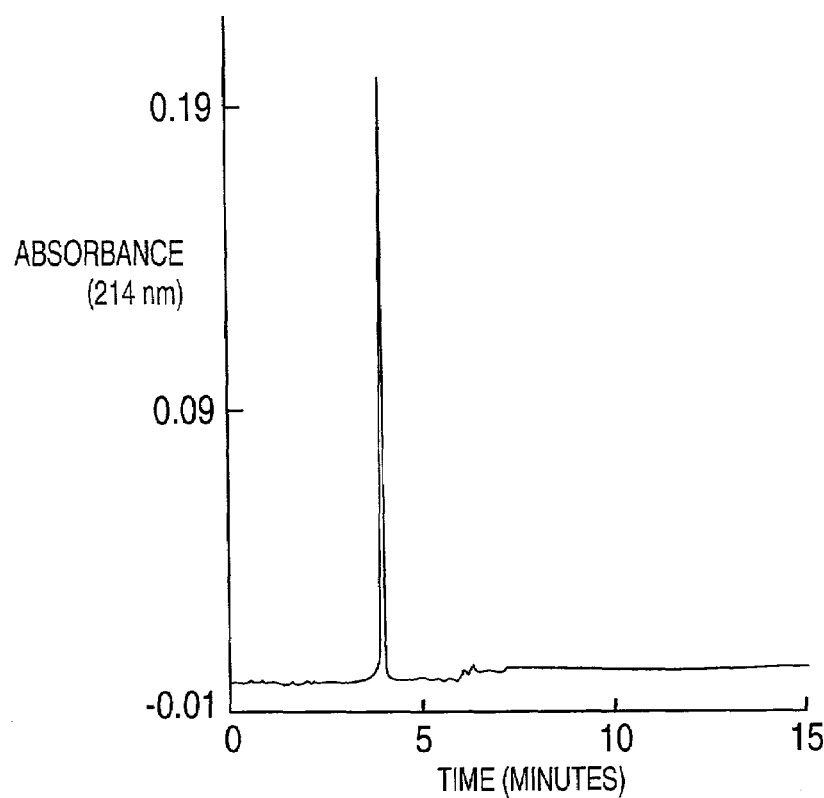
FIG. 6B illustrates an electropherogram of intact, dispersed *S. cerevisiae* using CE.

Tests were run with both aggregated and dispersed microbes. The specific microbes were *M. luteus*, and *S. cerevisiae*. FIGS. 5A and 5B illustrate the results for *M. luteus* while FIGS. 6A and 6B illustrate the results for *S. cerevisiae*. FIGS. 5A and 6A illustrate electropherograms for the respective aggregated microbes (*M. luteus, S. cerevisiae*) while FIGS. 5B and 6B illustrate the corresponding dispersed microbes. As can be seen, it is preferable to insure dispersion of microbes and avoid aggregates. As can be seen, the aggregated samples gave a plurality of peaks while the dispersed samples produced a single, definitive peak.

In order to break up the aggregates, an ultrasound bath was used, however, it has been found that such a bath does not always work, for example, with *Alcaligenes faecalis*.

The mobility ($\mu$) for each first peak was:

| FIG. | Mobility ($\mu$) cm/V |
|------|----------------------|
| 5A   | $-2.26 \times 10^{-4}$ |
| 5B   | $-2.32 \times 10^{-4}$ |
| 6A   | $-1.39 \times 10^{-4}$ |
| 6B   | $-1.44 \times 10^{-4}$ |

This example was run in a manner similar to Example 1, except the times and concentration of the wash fluids between each run was slightly different.

Figure 6C:
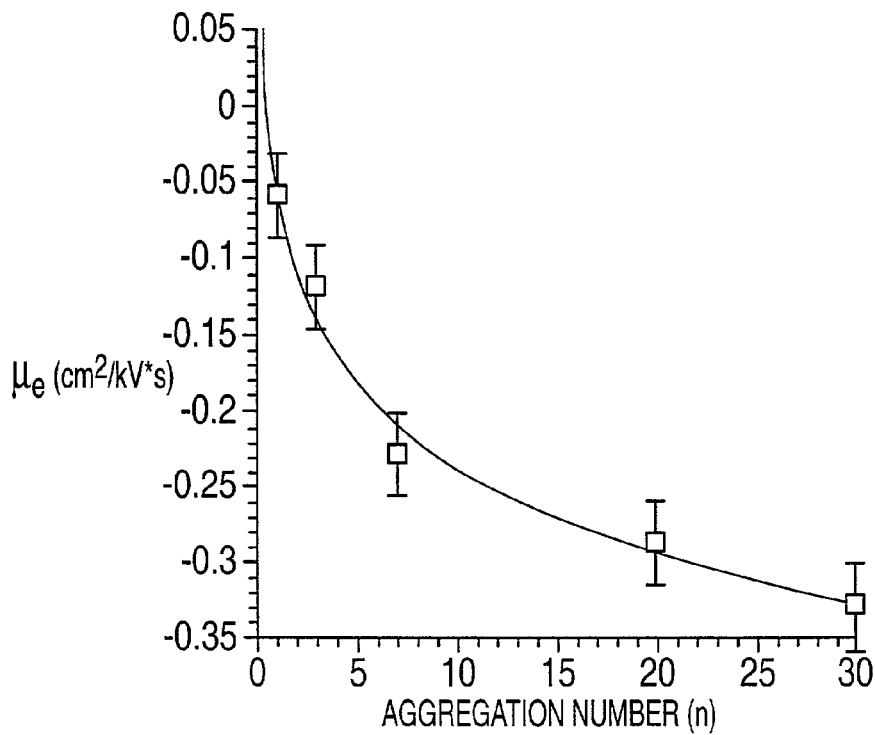
FIG. 6C illustrates the relationship between electrophoretic mobility and aggregation number for *S. cerevisiae*.
Figure 6D:
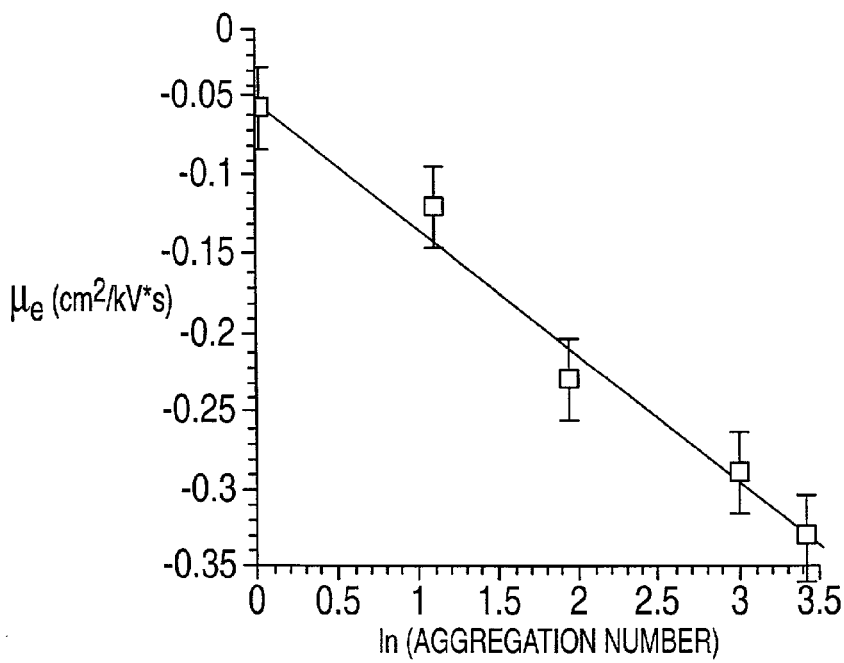
FIG. 6D illustrates the relationship between mobility and in aggregation numbers from FIG. 6C.

Individual aggregates can be examined to determine the quantity of microbes present. The relationship between the size of the cellular aggregate and its electrophoretic mobility was evaluated ($\mu_e$) There was a regular curvilinear relationship between $\mu_e$ and the aggregation number (n) of *S. cerevisiae* (FIG. 6C) as well as a corresponding linear relationship between $\mu_e$ and ln (n) (FIG. 6D). The equation for the best fit through cuve in FIG. 6C is: $n=(0.55)(10^{-12\mu_e})$ where $\mu_e$ is the electrophoretic mobility of the *S. cerevisiae* aggregate containing "n" cells.

Thus, using the process of the present invention, the appropriate aggregation number or size of any microbial aggregate represented by a peak in the corresponding electropherogram can be determined. Also, the aggregational distribution of the microbial population using the entire electropherogram can be determined using the present invention.

EXAMPLE 5

This example illustrates the use of capillary electrophoresis to separate and identify two viruses from a mixture thereof.

FIG. 7 illustrates the separation of *E. coli* Phage $T_4$ virus from $T_1$ virus. As can be seen, the two viruses were separated one from another and, because of the selectivity and efficiency of the separation, they were able to be identified.

The viruses used for this example were obtained from a conventional source and the capillary electrophoresis run with the polymer (PEO) in the same manner as detailed in Example 1 above except that the concentration of PEO was 20 to 40 times greater because the virus was so small.

EXAMPLE 6

This example illustrates the use of capillary electrophoresis to separate fungi.

FIG. 8A is the electropherogram for intact *Oidiodenran tenuissmum*, while FIG. 8B is the electropherogram for intact *Penicillium rotatum*. Because of the selectivity and efficiency of the separation, these fungi were able to be clearly identified.

The fungi were obtained from a conventional source and the capillary electrophoresis run with a polymer (PEO) in the same manner as detailed in Example 1 above.

EXAMPLE 7

This example illustrates using capillary isoelectric focusing to separate and identify individual, intact microbes from a mixture thereof and, specifically, a mixture of bacteria.

Figure 9:
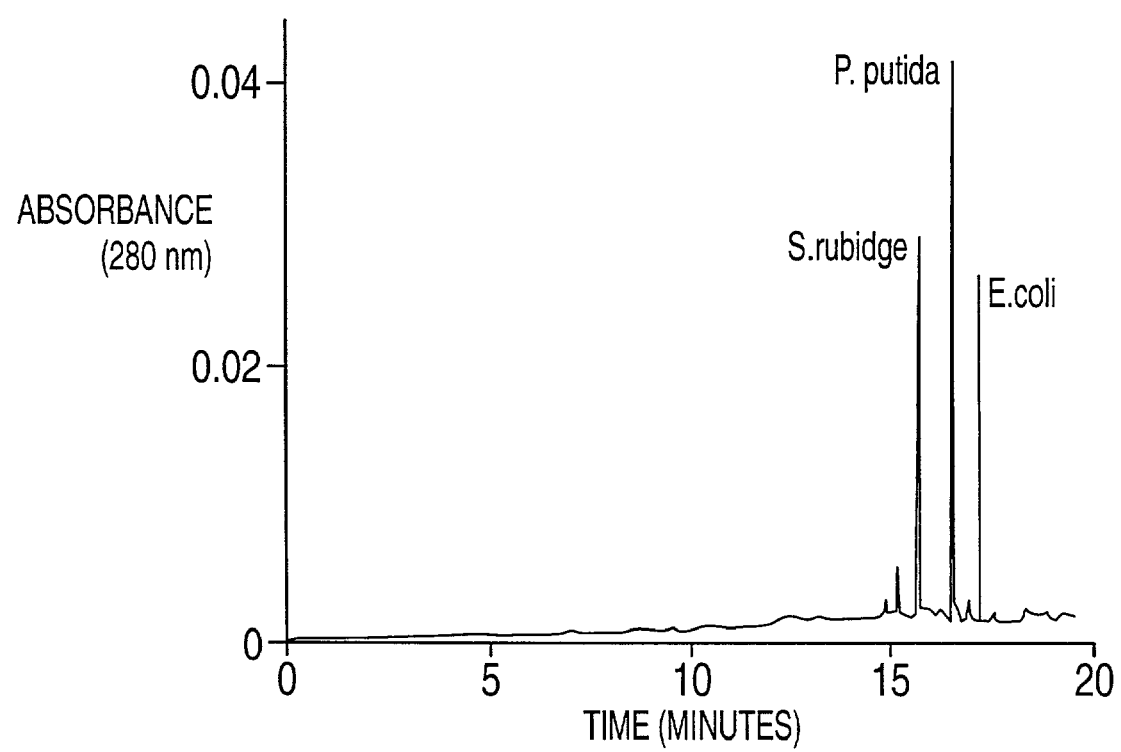
FIG. 9 illustrates an electropherogram of an intact mixture of microbes separated and identified in accordance with the present invention using capillary isoelectric focusing.

FIG. 9 illustrates the separation of the individual microbes from the mixture of microbes (*E. coli, P. putida*, and *S. rubidae*). Because of the efficiency and selectivity of the separation, each of the individual microbes were identified. The respective peaks in FIG. 9 have been labeled.

It should be noted that even though these three bacteria were similar in size (diameter) and identical in form (straight rods), they were able to be both separated and identified.

The microbes employed in this example were the ones identified above, under the heading Microbe Preparation. For the isoelectric focusing, each bacteria was prepared using 0.5–1.0 ml of the culture broth. They were pelleted for 3–5 min. using a centrifuge (Fisher Scientific Model 228) at 3400 rpm. The supernatant was removed and the cells washed to remove culture. The washing was repeated twice. The bacteria was then resuspended in dilute ampholyte, pH 3–10 (BIO-LYTE AMPHOLYTE from Bio-Rad, Hercules, Calif.).

Capillary isoelectric focusing was carried out using a Beckman P/ACE 5000 CE unit. The capillary tube was 50 m×47 cm (40 cm to the detector) coated silica capillary. The methylcellulose coating of the capillary is prepared by the procedure described in Hjerten, S. et al. Electrophoresis 1993, 14, 390–395. The pH gradient was generated with the ampholyte (BIO-LYTE AMPHOLYTE pH 3–10). The ampholyte was diluted with water to a final concentration of 0.5% V/V. The anolyte was 20 mM phosphoric acid while the catholyte was 20 mM sodium hydroxide. Before each separation the capillary tube was washed for 2 min with water and ampholyte. Samples were injected into the tube at 0.5 psi for 90 seconds followed by a second injection of ampholyte for 129 seconds. After focusing for 5 min (voltage 20 KV) samples were mobilized with low pressure (0.5 psi) rinse while the 20 KV voltage was maintained. Detection of analytes was carried out at 280 nm, using an on-line UV detector. All separations were carried out at 23° C. under thermostated conditions.

Typically, current initially increased sharply to about 4 μA and then decreased to 1 μA over the 5 min focusing period. The blind side of the tube, the part behind the detection window, was not blocked with a basic compound because the bacteria have an isoelectric point at lower pH values. Thus, there was no risk of focusing bacteria at the blind side of the tube.

EXAMPLE 8

This example illustrates diagnosis of a disease in accordance with the present invention and, specifically, a urinary tract infection.

Figure 10A:
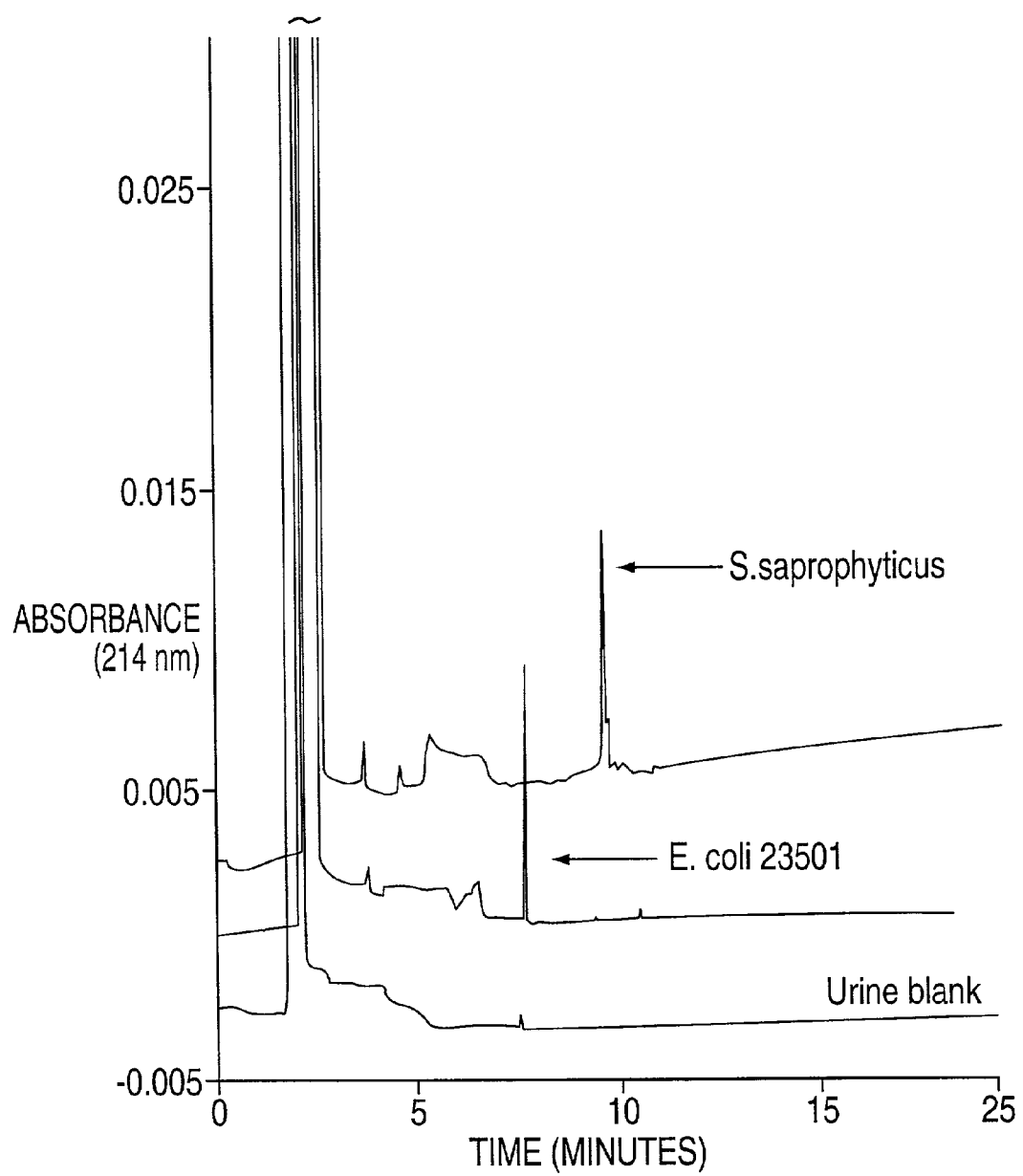
FIG. 10A illustrates an electropherogram of urine, and the separation and identification of bacteria from the urine in accordance with the present invention using CE.

FIG. 10A illustrates the separation and identification of bacterium in dilute urine using capillary electrophoresis in accordance with the present invention. *Escherichia coli* and *Staphylococcus saprohyticus* are the primary cause of urinary tract infections. As can be seen, the process of the present invention was able to distinguish between the two and produce high efficiencies, in some cases exceeding 1,000,000 plates/m, and short analysis times, less than 10 min.

Figure 10B:
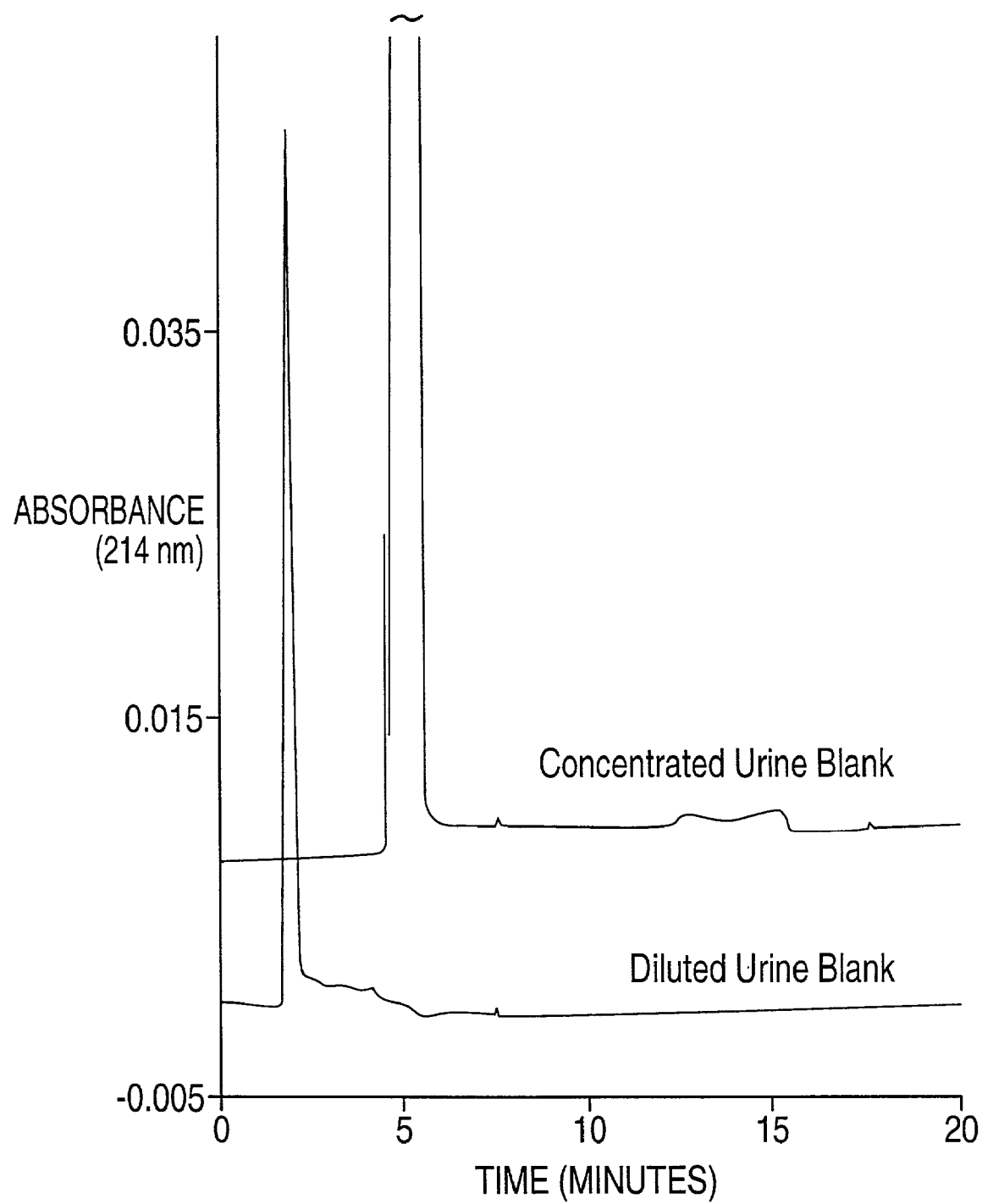
FIG. 10B illustrate electropherograms of both dilute and concentrated urine.

FIG. 10B illustrates the electropherogram for dilute versus concentrated urine. Since the constituents of urine vary widely in concentration depending on individuals, liquid intake, food intact, activity, health, etc., the urine concentration and makeup of itself must be taken into consideration, primarily because it effects the velocity of the EOF, more concentrated samples produce a lower EOF velocity.

Figure 10C:
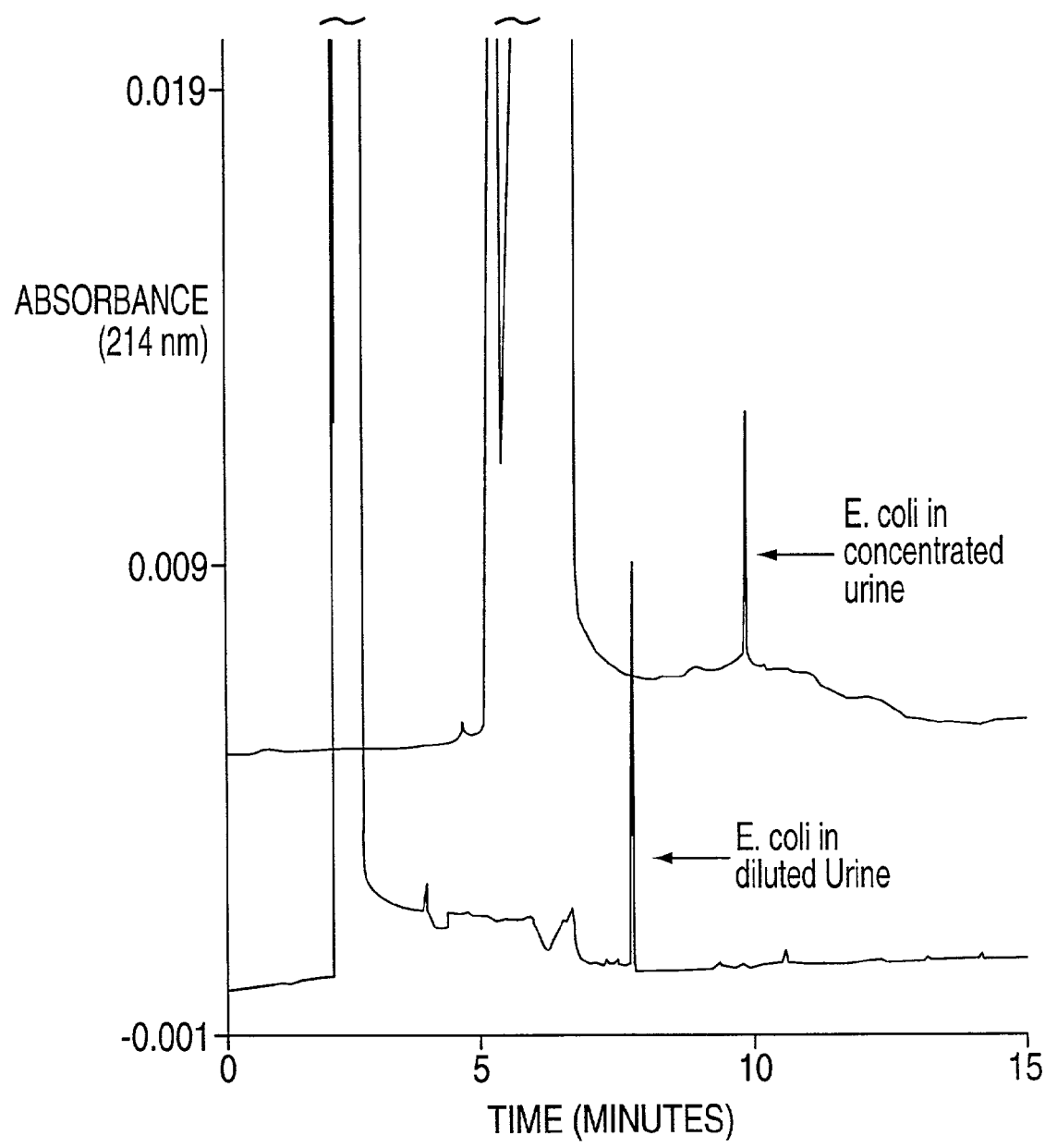
FIG. 10C illustrate electropherograms of *E-coli* in both dilute and concentrated urine.

FIG. 10C illustrates the different migration times, velocities, of the same bacteria for concentrated versus dilute urine. As can be seen, simple migration times should not, as a general rule, be used to identify a bacterium. The use of internal standards and electrophonetic mobility enhances accurate identification.

The bacteria, *Escherichia coli* 23501 and *Staphylococcus saprophyticus* were obtained from a conventional source. The urine was obtained from a healthy male and used to mix with the bacteria.

In order to perform the capillary electrophoresis the stock buffer of Example 1 above was used except it was diluted to 16:1 using deionized water and then adjusted to a pH of 9.0 using 0.1 NaOH. The polymer solution was prepared according to Example 1 above, except the PEO used had an average molecular weight (Mn) of 100,000, and instead of using an ultrasound bath, it was stirred for three hours. The running buffer was prepared from the dilute stock buffer and polymer solution to give a final polymer concentration of 0.0125%.

The infected urine was prepared by first dissolving the bacteria in 2 ml of the running buffer for 30 min, then pelleting the samples in a centrifuge for 3–5 min (Fischer Scientific Model 228) at 3400 rpm. The vials containing the bacteria were then shaken and centrifuged again. This process was repeated once and finally the washed bacteria was suspended in 1–2 ml of urine.

The capillary electrophoresis was performed as outlined in Example 1 above, except 1 N phosphoric acid was used in the wash process, and the samples were pressure injected for 20 s at 0.5 psi.

As will be appreciated, urine contains a number of non-microbial components such as urea, proteins, minerals (sodium, potassium, magnesium, zinc), sugars, etc.

EXAMPLE 9

This example illustrates employing the present invention to detect the presence of a microbe in a dietary supplement.

A commercial dietary supplement (sold by Schiff) used by individuals that are lactose intolerant was tested to determine the presence of *Lactobacillus acidophilus*.

Figure 12:
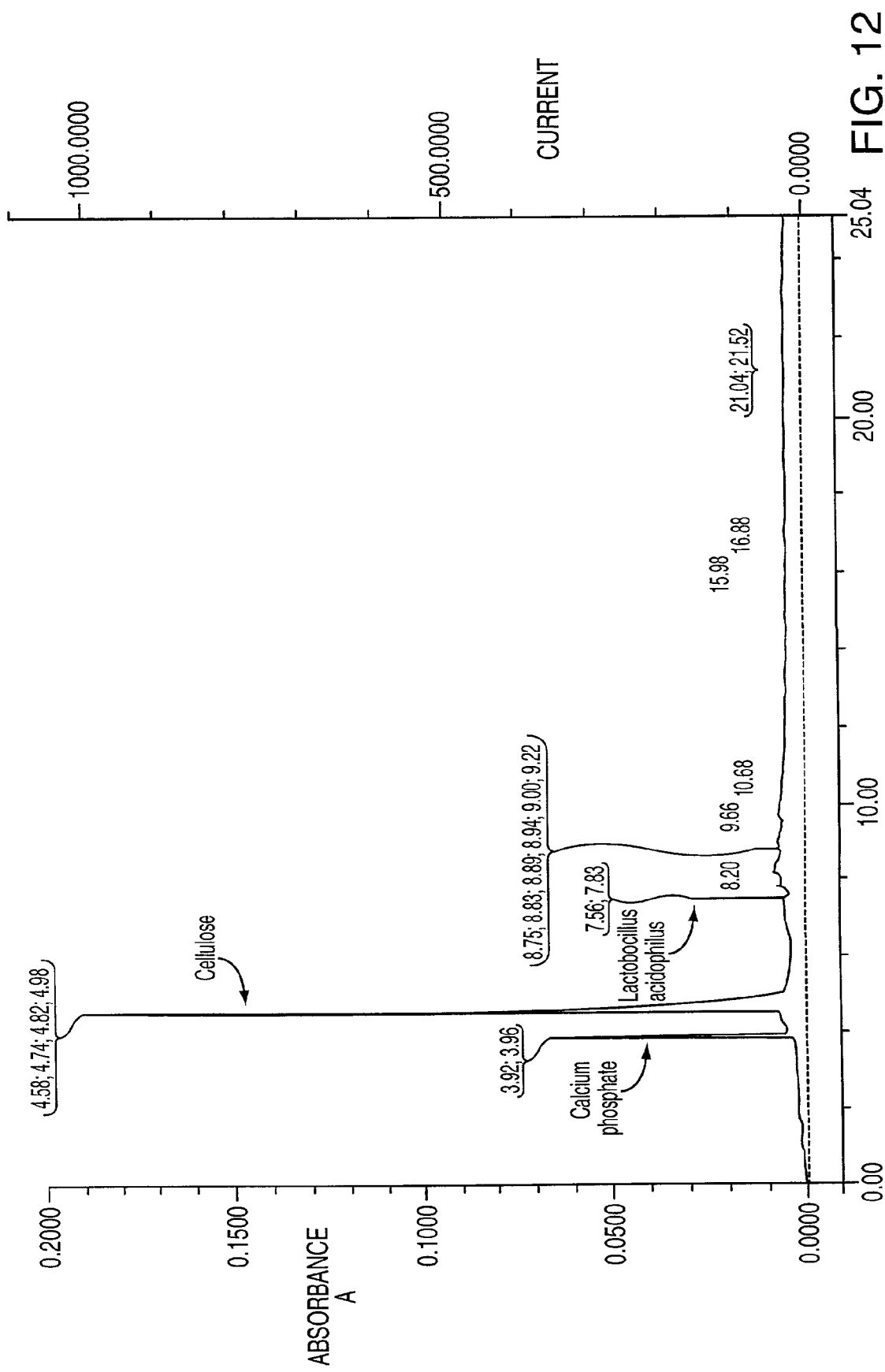
FIG. 12 illustrates an electropherogram of a dietary supplement containing cellulose, calcium phosphate and *Lactobacillus acidophilus*.

The sample was analyzed using capillary electrophoresis and FIG. 12 illustrates the results. The different components in the sample as detected were labelled, i.e. calcium phosphate, cellulose and *lactobacillus acidophillus*. The capillary electrophoresis was run using a buffer solution containing 0.56 mM tris(hydroxymethyl)-aminomethane, 0.56 mM boric acid and 0.013 mMEDTA (disodium ethylenediaminetetracetate) prepared by dissolving the appropriate amounts of each reagent in deionized water to yield a buffer of pH 8.4.

The polymer solution was prepared by adding PEO, Mn=600,000, to the buffer solution to give a final concentration of PEO of 0.0250%.

The sample was prepared by mixing a portion of the diet supplement into the buffer.

The capillary electrophoresis was run using a Beckman P/ACE 2100 coupled to a computer equipped with Gold data acquisition software. Fused-silica capillary tubes with a 100 μm i.d. were used. The running buffer was prepared from the buffer to provide a final polymer concentration of 0.0250%. The column was 27 cm in length, 20 cm window. The separation voltage was 12 KV at a temperature of 25° C. On-line detection of the bacterium was done at 280 nm.

As shown in FIG. 12, the microbe was separated from the other, non-microbial, components in the sample.

EXAMPLE 10

This example illustrates employing the present invention to detect a spore. Such spores are conventionally used in germ warfare because the spore will lay dormant in a bomb/missile warhead for years and, upon being released at the target site, start to grow.

Figure 13:
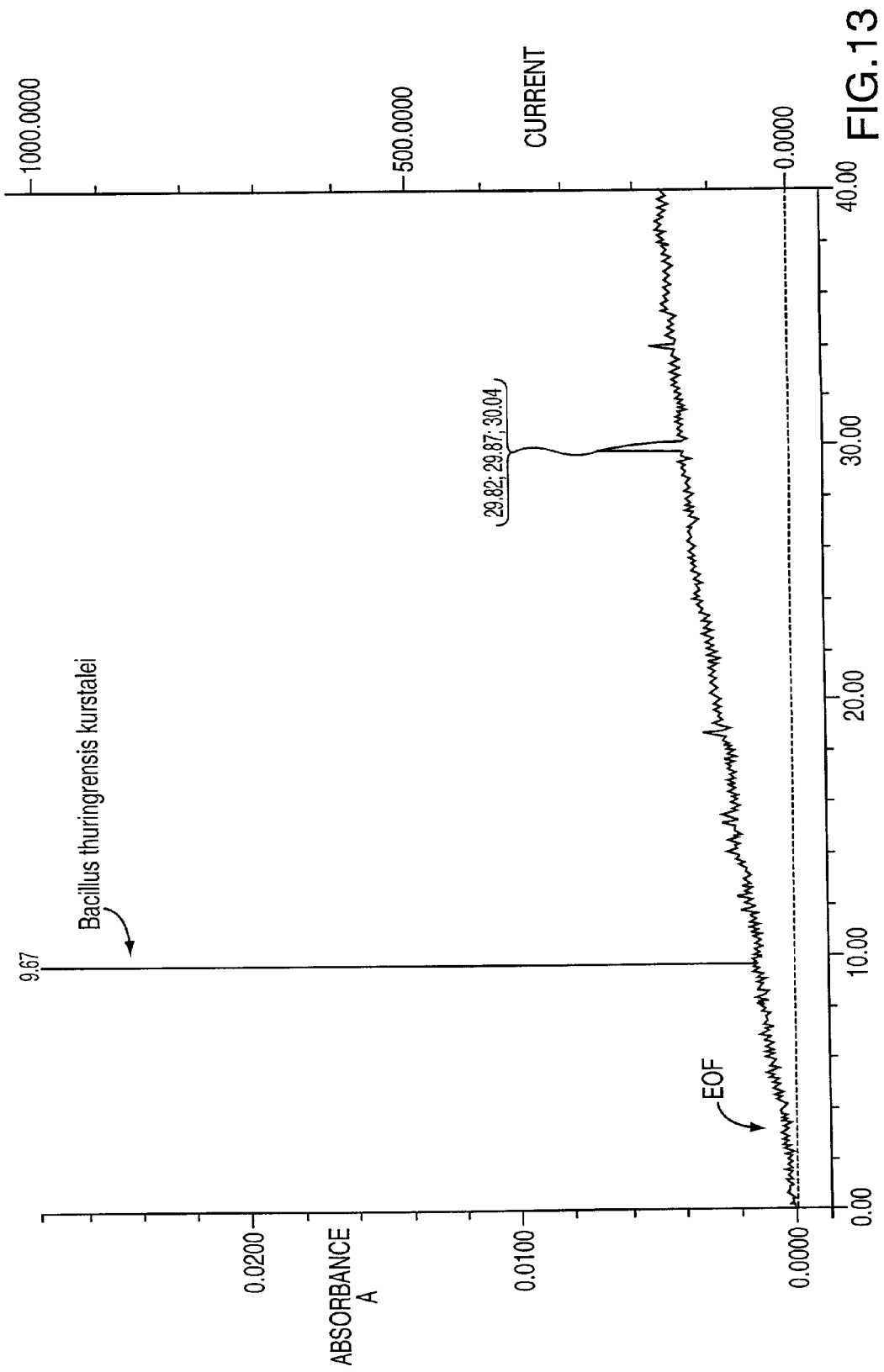
FIG. 13 illustrates an electropherogram of a sample containing a bacterial spore.
Figure 14A:
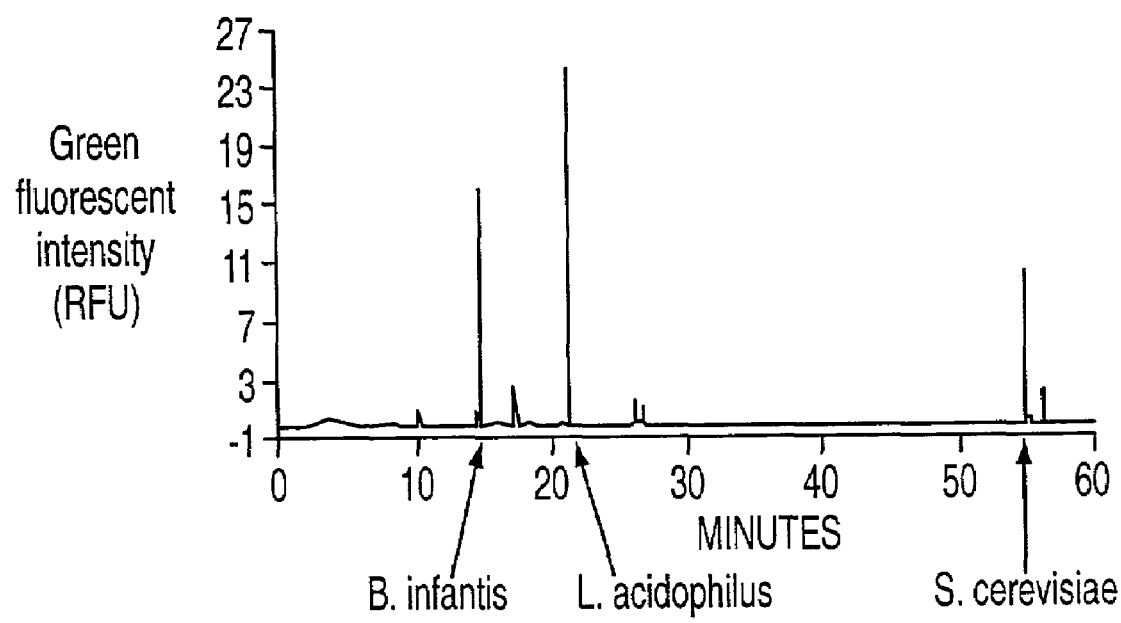
FIGS. 14A and 14B are electropherograms showing the simultaneous separation of *B. infantis, L. acidophilus*, and *S. cervasi*, and detection of live (green fluorescence) and dead (red fluorescence) cells.
Figure 14B:
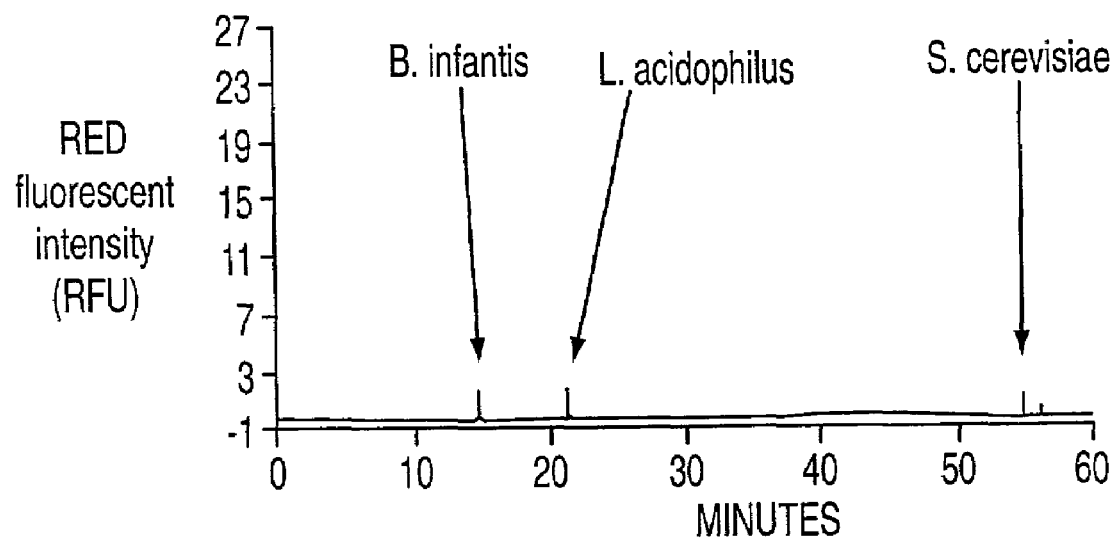

The sample contained *Bacillus thuringrensis kurstaki* and was detected as shown in FIG. 13.

The capillary electrophoresis was run as in Example 1 above except that the on-line detector was set for 280 nm.

EXAMPLE 11

This example illustrates both the separation and the quantification of viable microbes using capillary electrophoresis.

A mixture of individually stained *B. infantis, L. acidophilus*, and *S. cerevisiae* was prepared, and separated and the number of live and dead cells determined using capillary electrophoresis. The live cells fluoresced green while the dead cells fluoresced red.

FIG. 14A illustrates the green (live) fluoresced microbes and FIG. 14B illustrates the red (dead) fluoresced microbes. The peaks have been labeled with their respective microbes.

In order to quantify the live and dead cells, a standard curve that plot the ratio of green/red signals versus the percentage of live cells was prepared in a conventional manner. Such a plot is shown in FIG. 15.

Using the ratio of peak areas in FIGS. 14A and 14B, it was determined that the viability of *L. acidophilus* was 45 percent, *S. cervasai* was 43 percent, and *B. infantis* was <2 percent. The error in these determinations (% RSD, n=5) was 14 percent, 10 percent, and 16 percent, respectively.

The capillary electrophoresis was run using the diluted buffer and the running buffer of Example 1 above, except the polymer concentration in the running buffer was 0.025%.

The capillary electrophoresis (CE) separation was performed on a Beckman Coulter P/ACE MDQ capillary electrophoresis system equipped with 488 nm laser induced fluorescence (LIF) detector. Untreated fused silica capillary with a 100 μm i.d., used for the separation, was 30 cm in length (20 cm to detection window). The capillary was first rinsed for 0.5 minute with water, 5 minutes with 1N NaOH, and 0.5 minute with water. Then enough runs should be made in order to stabilize the inner capillary wall. Prior to each injection, the capillary was washed for 0.5 minute with water, 0.2 minute with IN NaOH, and 0.5 minute with water, followed by 2 minutes with running buffer. The running buffer was changed between each run. Separations were performed at 15 kV and a temperature of 25° C. The green and red fluorescent light was monitored simultaneously with a LIF detector, which was equipped with a proper green light filter and red light filter. Data was collected by P/ACE system MDQ software.

In order to make up the mixture, the individual microbes ere suspended in the running buffer and 50 μl of each solution diluted to 3.0 ml with the running buffer. Next, they were stained separately with 1 μl of mixed green and red dye (1:1 v/v). The two bacteria, *L. acidophilus* and *B. infantis*, were incubated in the dark for 15 minutes while the yeast, S. cervisiae, was incubated in the dark for 40 minutes. After incubation, the three suspensions were mixed together just before injection.

The mixture was injected for 10 seconds at 0.5 psi. A 520 nm band pass filter and a 663 nm long pass filter were used to monitor the green and red light, respectively.

Figure 15:
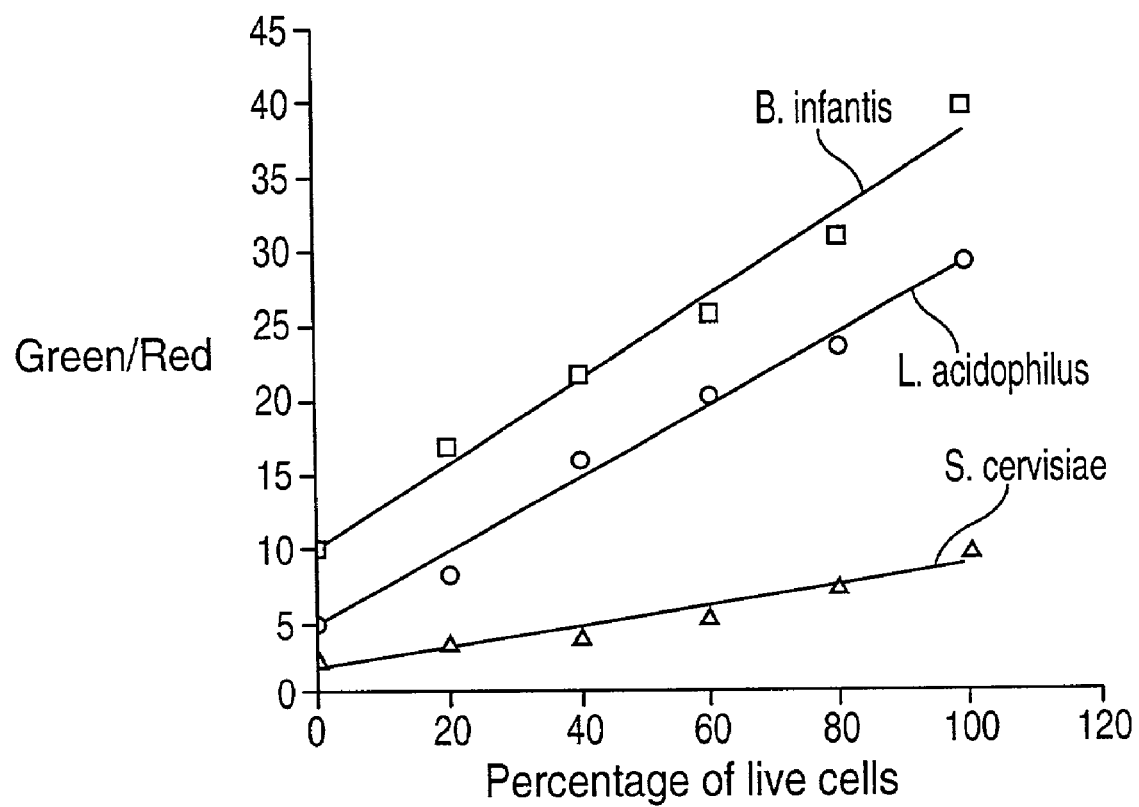
FIG. 15 are standard viability curves for *B. infantis, L. acidophilus*, and *S. cervasi*.

In order to obtain the data and plot of FIG. 15, live/dead cells for each microbe, 6 different proportions of fresh and properly fixed cell suspensions with a total volume of 50 μl were mixed and diluted to 3.0 ml. Therefore, the ratios of live/dead cells in solution were 0:100, 20:80, 40:60, 60:40, 80:20 and 100:0. All cells were stained with 1 μl of mixture of green and red dyes (1:1, v/v). In a separate experiment, yeast cells were labeled with 1 μl FUN-1™ stain. After the FUN-1™ stain was added to the yeast solution, the sample was mixed thoroughly and incubated at 30° C. in the dark for 30 minutes. When loaded with FUN-1™ stain, dead yeast cells exhibit extremely bright, diffuse, green-yellow fluorescence, while metabolically active cells were marked with distinct orange-red fluorescence when observed under the fluorescence microscope. Each sample was injected for 10 seconds at low pressure and measured 3–6 times. A 520 nm band pass filter and 663 nm long pass filter were the green light filter and red light filter, respectively. The calibration curves were obtained by plotting ratios of green to red fluorescent intensities were ratios of live dead cells of the same sample.

The microbes were obtained from conventional sources. Each microbe was grown in a conventional manner. The bacteria cells were allowed to grow in Nutrient Broth at 37° C. on a shaker at 600 rpm for 16–20 hours. The starting culture of yeast was transferred from solid agar to YPD medium (10 g yeast extract, 20 g peptone, and 20 g dextrose/liter) and grown at 30° C. on a shaker at 300 rpm for 12–15 hours. Samples from cultures were obtained by removing 4–6 ml of liquid culture and pelleting the cells in a centrifuge (Fisher model 228, Pittsburgh, Pa., USA) at 3400 rpm. The supernatant was decanted and the cells were washed with 3–4 ml of running buffer and pelleted again. After another wash, the cells were dispersed in running buffer. The cell concentration was determined from the optical density of the solution at 670 nm with a UV/Vis Spectrophotometer (model U-200, Hitachi Instruments, Inc.). The L. acidophilus suspension was adjusted to ~0.250 $OD_{670}$ (~$3 \times 10^7$ cells/ml). B. infantis suspension to viabilities of fresh cultures of three microbes were checked by flow cytometry (Beckman Coulter EPICS XL-MCL), which showed that over 90% cells of fresh cultures in solution were live. Dead cells of bacteria were obtained by suspending cells in acetone at −20° C. overnight (~10 hours), then washing twice with running buffer to remove residue acetone and re-suspending in running buffer.

In order to stain the microbes a LIVE/DEAD BALLIGHT BACTERIAL VIABILITY kit and a LIVE/DEAD YEAST VIABILITY kit from Molecular Probes, Inc. (Eugene, Oreg., USA) was used. The dyes used for bacteria were SYTO 9 green fluorescent nucleic acid stain (3.34 mM) and red fluorescent nucleic acid stain, propidium iodide (20 mM). The dye used for the yeast was FUN-1™ stain (10 mM). All stains were dissolved in DMSO.

In CE-LIF, the total luminescence is measured and it must be proportional to the number of cells present. Thus, all cells must be saturated with the dye to an extent that the addition of more dye will not alter their fluorescence. In this Example, it was found that this amounts to $\leq 1$ μM green fluorescent dye for $10^7$ cells/ml and $\leq 7$ μM red fluorescent dye for $10^7$ cells/ml. These concentrations are somewhat higher than those used when staining cells for microscopy, etc.

Both the correction for spectral overlap and the viability determination are accomplished using a standard curve that plots the ratio of the green/red signal versus the percentage of live cells, see FIG. 15. It is important that the standard curves be accurate and representative of the unknown cells to be measured. Specifically, standard dead or fixed cells must be obtained that absorb the dye in the same way, and amounts as the cells from the unknown sample that have died naturally. Yeast cells are a case in point. Cells that have been fixed by different procedures absorb different amounts of propidium iodide.

It has been found that SYTO9 propidium iodide which is usually used for bacterial also worked very well for yeasts to determine their viability in accordance with the present invention.

EXAMPLE 12

This example illustrates detecting the viability of microbes in the dietary supplement tested in Example 9 above.

Figure 16A:
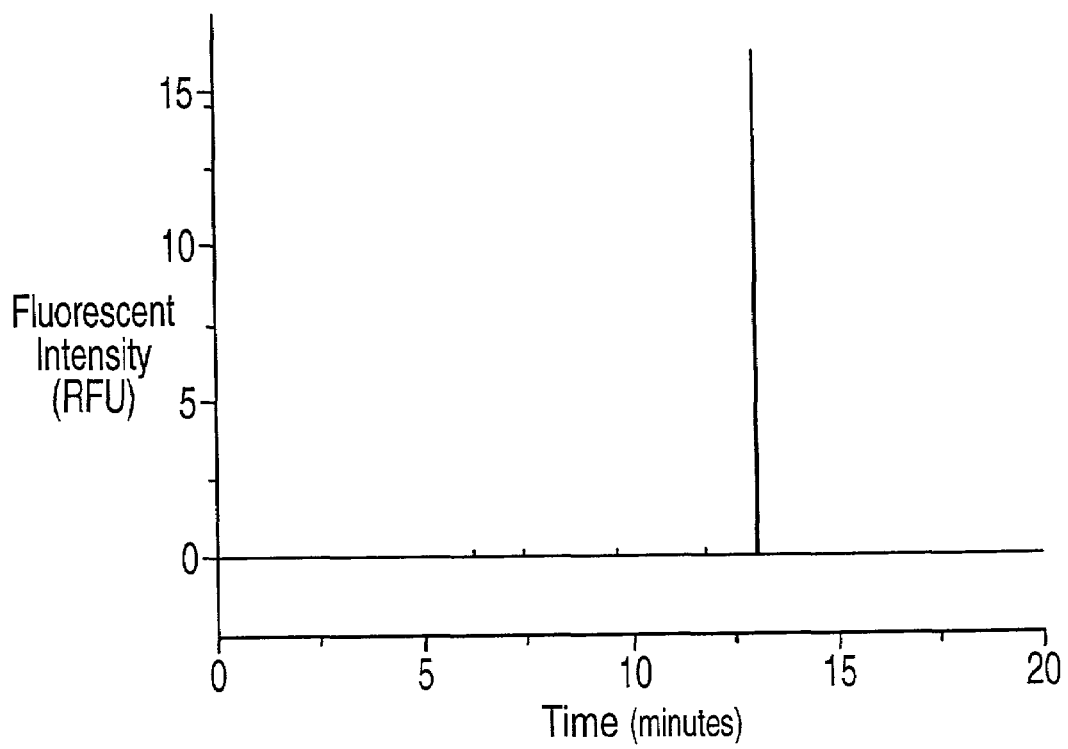
FIGS. 16A and 16B are electropherograms which quantify the number of live (16A) versus dead (16B) *L. acidophilus* cells in a commercial dietary supplement.
Figure 16B:
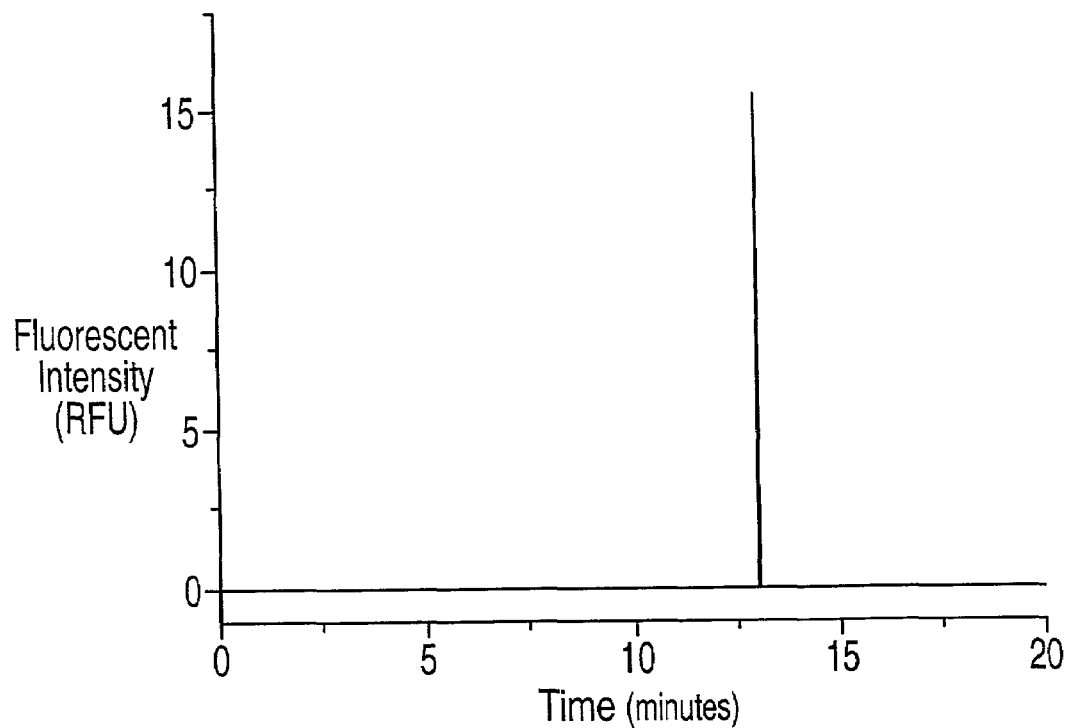

Tablets of the dietary supplement were tested to determine the percent of viable L. acidophilus cells in the tablets. FIGS. 16A and 16B are CE/LIF electropherograms generated by simultaneously monitoring (FIG. 16A) green fluorescence of viable cells (520 nm) and (FIG. 16B) red fluorescence of the dead cells (<662 nm) obtained from the Schiff tablets. The ratio of viable to non-viable cells can be obtained. Analysis shows that only about 60% of the L. acidophilus cells in the Schiff tablet samples are viable.

The materials of Example 11 were employed in this test.

Samples were prepared by dissolving one Schiff tablet in 20 ml running buffer. Three ml aliquots of cloudy solution were taken as samples. Approximately 1 μl of 20 mM propidium iodide and 10 μl 3.34 μM SYTO 9 solution was added to a 3 ml sample solution. The sample was incubated in the dark for 30 min. Generally, SYTO 9 stain labels all bacteria in a population—those with intact membranes and those with damaged membranes. In contrast, propidium iodide penetrates only bacteria with damaged membranes, causing a reduction in the SYTO 9 stain fluorescence when both dyes are present. Thus, with an appropriate mixture of SYTO 9 and propidium iodide stains, live bacteria with intact cell membranes stain fluorescent green, whereas dead bacteria with damaged membranes stain fluorescent red.

Viability determination was completed on a Beckman Coulter P/ACE MDQ capillary electrophoresis system, equipped with 488 nm laser induced fluorescence (LIF) detector. The sample was injected for 5–10 s at 0.5 psi. The separations were performed at 15 kV and a temperature of 25° C. Green and red fluorescent light were monitored simultaneously with the LIF detector, which is equipped with a 520 nm band pass filter and a 663 nm long pass filter, respectively. Data were collected with P/ACE system MDQ software.

The ratio of green fluorescence peak area to the red fluorescence peak area can be correlated to the ratio of live cells to dead cells in a pill after correcting for spectral overlap and normalizing the peak areas to known concentrations of live and dead cells. Relatively high concentrations of the dyes are used (compared to biological staining procedures) in order to maximize staining of the cells and produce consistent results. The CE-LIF cell viability results were confirmed by flow cytometry using a Beckman Coulter EPICS XL-MCL instrument.

Thus, in this way, the viability of the cells in the dietary supplement were tested. Such a test can be used as a quality control test for foods and drugs which contain microbes.

EXAMPLE 13

This example illustrates measuring the affinity or binding of molecules (drugs) to microbes.

Figure 17A:
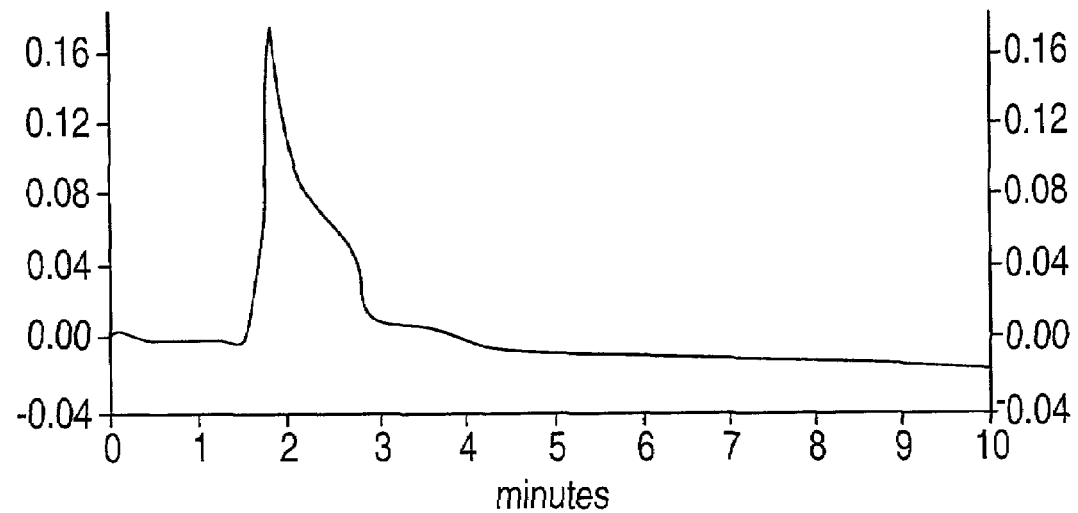
FIGS. 17A and 17B are electropherograms which demonstrate the affinity of an antibiotic for a microbe.
Figure 17B:
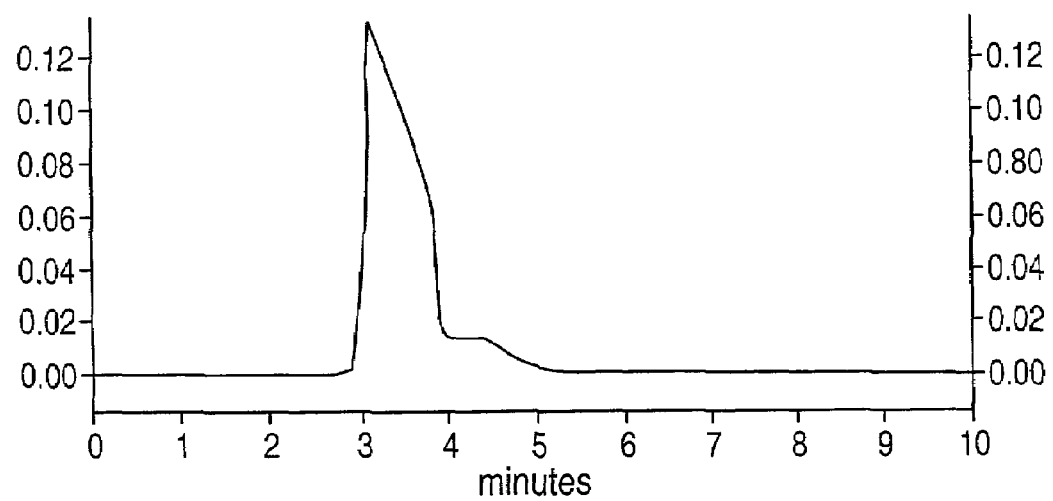

Using *M. luteus* (bateria) and vancomycin (antibiotic), a mixture is formed and injected into a column of capillary electrophoresis system of Example 1. FIGS. 17A and 17B illustrate the different binding. In FIG. 17A, 3.3 mg/ml of vancomycin was used with 0.67 mg/ml of *M. lutens*. In FIG. 17B, 2.0 mg/ml of vancomycin was used with 0.8 mg/ml of *M. lutens*.

As can be seen, the lower percent of drug to microbe in FIG. 17B resulted in a different electropherogram.

It will be understood that the claims are intended to cover all changes and modifications of the preferred embodiments of the invention herein chosen for the purpose of illustration which do not constitute a departure from the spirit and scope of the invention.

What is claimed is:

1. A process for separating and identifying intact microbes while maintaining the microbes/cells intact comprising:
    (a) obtaining a sample comprising one or more intact microbes/cells from a substrate containing said microbes/cells;
    (b) introducing said sample into a passageway having a moving fluid therein;
    (c) separating said one or more microbes/cells in said moving fluid by means of electrophoresis so as to separate said one or more microbes/cells in said moving fluid and to separate one from another and from any other components in said sample while maintaining said microbes/cells intact; and
    (d) analyzing said separated intact microbes/cells so as to identify said microbes/cells,
    wherein said moving fluid comprises a waterbased solution and a dilute water soluble polymer that separates said microbes in said passageway during said separating step.

2. The process of claim 1 wherein said passageway is a conventional capillary tube or a microchip fluidic device.

3. The process of claim 1 wherein said analyzing is conducted by spectroscopy, mass spectrometry or electrochemical means.

4. The process of claim 1 wherein the substrate is a foodstuff, a dietary supplement, water, animal, plant, soil, or air.

5. The process of claim 1 wherein said water soluble neutral polymer is polyethylene oxide, polyethylene glycol, polyvinyl alcohol, linear polyacrylamide, hydroxypropylcellulose, hydroxyethylcellulose, methylcellulose, amylase or dextrin.

6. A process for diagnosing a disease caused by microbes comprising:
    (a) obtaining a sample containing one or more intact microbes from an organism stricken with a disease caused by said microbes;
    (b) introducing said sample into a passageway having a moving fluid therein;
    (c) separating said one or more microbes in said moving fluid by means of electrophoresis so as to separate said one or more microbes in said moving fluid and to separate one from another and from other components in said sample while maintaining said microbes intact;
    (d) analyzing said separated intact microbes so as to identify said microbes; and
    (e) associating said microbe with a disease so as to diagnose said disease,
    wherein said fluid comprises a waterbased solution and a dilute water soluble polymer that separates said microbes in said passageway during said separating step.

7. The process of claim 6 wherein said passageway is a conventional capillary tube or a microchip system.

8. The process of claim 6 wherein the organism is a plant or an animal.

9. The process of claim 6 wherein said water soluble neutral polymer is polyethylene oxide, polyethylene glycol, polyvinyl alcohol, linear polyacrylamide, hydroxypropylcellulose, hydroxyethylcellulose, methylcellulose, amylase or dextrin.

10. A process for determining the binding affinity of a drug/other substance with a microbe/cell comprising:
    (a) obtaining a sample comprising one or more intact microbes/cells from a substrate containing said microbes/cells;
    (b) combining the sample with a drug or other substance in a fluid media to form a suspension and to allow said microbe/cell to bind with said drug/other substance;
    (c) introducing said suspension into a passageway having a moving fluid therein;
    (d) subjecting said suspension to electrophoresis so as to separate said microbes/cells, said drug/other substance and bound microbes/cells-drug/other substance in said moving fluid and to separate one from another while maintaining said microbes/cells, said drug/other substance and said bound microbes/cells-drug/other substance intact; and
    (e) analyzing said separated, intact bound microbes/cells-drug/other substance to determine their affinity for each other,
    wherein said moving fluid comprises a water-based solution and a dilute water soluble polymer that separates said microbes/cells, said drug/other substance and said bound microbes/cells-drug/other substance in said passageway during said subjecting step.

11. The process of claim 10 wherein drug/other substance is an antibiotic or a prion.

12. The process of claim 10 wherein said substrate is an animal.

13. The process of claim 10 wherein said passageway is a capillary tube or microfluidic device.

14. The process of claim 10 wherein said water soluble neutral polymer is polyethylene oxide, polyethylene glycol, polyvinyl alcohol, linear polyacrylamide, hydroxypropylcellulose, hydroxyethylcellulose, methylcellulose, amylase or dextrin.

15. A process for determining the viability of microbes/cells comprising:
    (a) obtaining a sample containing one or more intact microbes/cells from a substrate containing said microbes/cells;
    (b) dying said sample with a dye that causes viable microbes/cells to be distinguished from non-viable microbes/cells;
    (c) introducing said dyed sample into a passageway having a fluid therein;

(d) separating said one or more microbes/cells in said moving fluid by means of electrophoresis so as to separate said one or more microbes/cells in said moving fluid and to separate one from another and from other components in said sample while maintaining said microbes/cells intact; and (e) analyzing said separated intact microbes/cells so as to identify viable microbes/cells from nonviable microbes/cells based on said dye, wherein said moving fluid comprises a water-based solution and a dilute water soluble polymer that separates said microbes/cells in said passageway during said separating step.

16. The process of claim 15 wherein said passageway is a conventional capillary tube or a microchip capillary system.

17. The process of claim 15 wherein said water soluble neutral polymer is polyethylene oxide, polyethylene glycol, polyvinyl alcohol, linear polyacrylamide, hydroxypropylceliulose, hydroxyethyicelluiose, methylcellulose, amylase or dextrin.

18. A process for diagnosing a disease caused by microbes comprising:

(a) obtaining a sample containing one or more intact microbes from an organism stricken with a disease caused by said microbes;

(b) introducing said sample into a passageway having a fluid therein;

(c) separating said one or more microbes in said fluid by capillary isoelectric focusing so as to cause said one or more microbes to move in said fluid and to separate one from another and from other components in said sample while maintaining said microbes intact;

(d) analyzing said separated intact microbes so as to identify said microbes; and (e) associating said microbe with a disease so as to diagnose said disease, wherein said fluid comprises an ampholyte that focuses said microbes in said passageway during said separating step.

19. A process for determining the binding affinity of a drug/other substance with a microbe/cell comprising:

(a) obtaining a sample comprising one or more intact microbes/cells from a substrate containing said microbes/cells;

(b) combining the sample with a drug or other substance in a fluid media to form a suspension and to allow said microbe/cell to bind with said drug/other substance;

(c) introducing said suspension into a passageway having a fluid therein;

(d) subjecting said suspension to capillary isoelectric focusing so as to cause said microbes/cells, said drug/other substance and hound microbes/cells-drug/other substance to move in said fluid and to separate one from another while maintaining said microbes/cells, said drug/other substance and said bound microbes/cells-drug/other substance intact; and (e) analyzing said separated, intact hound microbes/cells-drug/other substance to determine their affinity for each other, wherein said fluid comprises an ampholyte that focuses said microbes/cells, said drug/other substance and said bound microbes/cells-drug/other substance in said passageway during said subjecting step.

20. A process for determining the viability of microbes/cells comprising:

(a) obtaining a sample containing one or more intact microbes/cells from a substrate containing said microbes/cells;

(b) dying said sample with a dye that causes viable microbes/cells to be distinguished from non-viable microbes/cells;

(c) introducing said dyed sample into a passageway having a fluid therein;

(d) separating said one or more microbes/cells in said fluid by capillary isoelectric focusing so as to cause said one or more microbes/cells to move in said fluid and to separate one from another and from other components in said sample while maintaining said microbes/cells intact; and (e) analyzing said separated intact microbes/cells so as to identify viable microbes/cells from non-viable microbes/cells based on said dye, wherein said fluid comprises an ampholyte that focuses said microbes/cells in said passageway during said separating step.

* * * * *